US007081568B2

(12) United States Patent
Misra et al.

(10) Patent No.: US 7,081,568 B2
(45) Date of Patent: Jul. 25, 2006

(54) TRANSGENIC PLANTS EXPRESSING TEMPORIN PEPTIDES

(75) Inventors: Santosh Misra, Victoria (CA); William W. Kay, Victoria (CA)

(73) Assignee: University of Victoria Innovation and Development Corporation, Victoria (CA)

( * ) Notice: Subject to any disclaimer, the term of this patent is extended or adjusted under 35 U.S.C. 154(b) by 80 days.

(21) Appl. No.: 10/719,623

(22) Filed: Nov. 20, 2003

(65) Prior Publication Data

US 2004/0073977 A1 Apr. 15, 2004

Related U.S. Application Data

(62) Division of application No. 09/936,885, filed as application No. PCT/CA00/00288 on Mar. 16, 2000, now Pat. No. 6,835,868.

(60) Provisional application No. 60/125,072, filed on Mar. 17, 1999.

(51) Int. Cl.
*A01H 5/00* (2006.01)
*C12N 15/82* (2006.01)

(52) U.S. Cl. .................. 800/301; 800/279; 800/288

(58) Field of Classification Search ............... 800/301, 800/298, 279, 288
See application file for complete search history.

(56) References Cited

U.S. PATENT DOCUMENTS

| 4,956,282 | A | 9/1990 | Goodman et al. | ........ 435/69.51 |
|---|---|---|---|---|
| 5,424,395 | A | 6/1995 | Bascomb et al. | ............ 530/326 |
| 5,593,866 | A | 1/1997 | Hancock et al. | ............ 435/69.7 |
| 5,597,945 | A | 1/1997 | Jaynes et al. | ................ 800/301 |
| 5,597,946 | A | 1/1997 | Jaynes et al. | ................ 800/279 |
| 5,707,855 | A | 1/1998 | Hancock et al. | ........ 435/252.33 |
| 6,025,326 | A | 2/2000 | Steinberg et al. | .............. 514/2 |
| 6,310,176 | B1 * | 10/2001 | Barra et al. | .................. 530/300 |

FOREIGN PATENT DOCUMENTS

| CN | 1249310 A | 4/2000 |
|---|---|---|
| EP | 0497366 A | 8/1992 |
| EP | 0552559 A | 7/1993 |
| EP | 0798381 A | 10/1997 |
| WO | WO 9415961 | 7/1994 |
| WO | WO 9518855 A | 7/1995 |
| WO | WO 9628559 A | 9/1996 |
| WO | WO 9806860 A | 2/1998 |
| WO | WO 9825961 A | 6/1998 |
| WO | WO 9840401 A | 9/1998 |
| WO | WO 9850543 A | 11/1998 |
| WO | WO 9906564 A | 2/1999 |
| WO | WO 0026344 A | 5/2000 |
| WO | WO 0031279 A | 6/2000 |

OTHER PUBLICATIONS

Simmaco et al 1996, European Journal of Biochemistry 242:788-792.*
Accession No. X97609, NCBI, NIH, Bethesda, MD USA database.
Accession No. U60601, NCBI, NIH, Bethesda, MD USA database.
Accession No. X67340, NCBI, NIH, Bethesda, MD USA database.
Accession No. X89202, NCBI, NIH, Bethesda, MD USA database.
Accession No. L39641, NCBI, NIH, Bethesda, MD USA database.
Accession No. U48795, NCBI, NIH, Bethesda, MD USA database.
Accession No. U95002, NCBI, NIH, Bethesda, MD USA database.
"Potato Soft Rot Reduced by Demeter Genes," PRNewswire, Demeter BioTechnologies, Ltd. (OTC Bulletin Board: DBOT), Jul. 9, 1997.
"Demeter BioTechnologies, Ltd. Licenses Broad Patent Rights for Disease Resistant Plants," PRNewswire, Demeter BioTechnologies, Ltd. (OTC Bulletin Board: DBOT), Jun. 10, 1997.
Allefs et al., "*Erwinia* Soft Rot Resistance of Potato Cultivars Expressing Antimicrobial Peptide Tachyplesin I," *Mol. Breeding* 2:97-105 (1996).
Charpentier et al., "Structure, Synthesis, and Molecular Cloning of Dermaseptins B, a Family of Skin Peptide Antibiotics," *J. Biol. Chem.* 273:14690-14697 (1998).
Fleury et al., "Synthesis, Antimicrobial Activity and Gene Structure of Novel Member of the Dermaseptin B Family," *Biochimica et Biophysica Acta* 1396:228-236 (1998).
Florack et al., "Expression of Giant Silkmoth Cecropin B Genes in Tobacco," *Transgenic Res.* 4:132-141 (1995).
Hancock et al., "Cationic Peptides: A New Source of Antibiotics," *TIBTECH* 16:82-87 (1998).
Jaynes et al., "Expression of a Cecropin B Lytic Peptide Analog in Transgenic Tobacco Confers Enhanced Resistance to Bacterial Wilt Caused by *Pseudomonas solanacearum,*" *Plant Sci.* 89:43-53 (1993).
Mastrangelo et al., "Overcoming Apoptosis: New Methods for Improving Protein-Expression Systems," *TIBTECH* 16:88-95 (1998).
Mor al., "The NH-2-Terminal Alpha-Helical Domain 1-18 of Dermaseptin is Responsible for Antimicrobial Activity," *J. Biol. Chem.* 269:1934-1939 (1994).

(Continued)

Primary Examiner—David H Kruse
(74) Attorney, Agent, or Firm—Klarquist Sparkman, LLP

(57) ABSTRACT

Transgenic plants that express temporin peptides are disclosed. In certain embodiments, these plants have enhanced, broad-spectrum pathogen resistance and are useful as agricultural or horticultural crops. In other embodiments, the plants are used to produce large quantities of the temporin peptide.

32 Claims, 3 Drawing Sheets

OTHER PUBLICATIONS

Mor et al., "The Vertebrate Peptide Antibiotics Dermaseptins Have Overlapping Structural Features but Target Specific Microorganisms," *J. Biol. Chem. 269*:31635-31641 (1994).

Norelli et al., "Transgenic 'Malling 26' Apple Expressing the Attacin E Gene Has Increased Resistance to *Erwinia amylovora*," *Euphytica 77*:123-128 (1994).

Okamoto et al., "Enhanced Expression of an Antimicrobial Peptide Sarcotoxin IA by GUS Fusion in Transgenic Tobacco Plants," *Plant Cell Physiol. 39*:57-63 (1998).

Piers et al., "Recombinant DNA Procedures for Producing Small Antimicrobial Cationic Peptides in Bacteria," *Gene 134*:7-13 (1993).

Simmaco et al., "Temporins, Antimicrobial Peptides from the European Red Frog *Rana temporaria*," *European J. Biochem. 242*:788-792 (1996).

Strahilevitz et al., "Spectrum of Antimicrobial Activity and Assembly of Dermaseptin-b and Its Precursor Form in Phospholipid Membranes," *Biochem. 33*:10951-10960 (1994).

Wechselberger, "Cloning of cDNAs Encoding New Peptides of the Dermaseptin-Family," *Biochimica et Biophysica Acta 1388*:279-283 (1998).

Hightower et al., "The Expression of Cecropin Peptide in Transgenic Tobacco Does Not Confer Resistance to *Pseudomonas syringae* pv *tabaci*," *Plant Cell Rep. 13*295-299 (1994).

Pang et al., "Expression of a Gene Encoding a Scorpion Insectotoxin Peptide in Yeast, Bacteria and Plants," *Gene 116*:165-172 (1992).

* cited by examiner

TRANSGENIC PLANTS EXPRESSING TEMPORIN PEPTIDES

CROSS REFERENCE TO RELATED APPLICATIONS

This is a division of U.S. application Ser. No. 09/936,885, filed Sep. 17, 2001 now U.S. Pat. No. 6,835,868, which is the U.S. National Stage of International Application No. PCT/CA00/00288, filed Mar. 16, 2000, which was published in English under PCT Article 21(2), which claims the benefit of U.S. Provisional Application No. 60/125,072, filed Mar. 17, 1999. All three applications are incorporated herein in their entirety.

FIELD OF THE INVENTION

This invention relates to plants that are genetically engineered to express one or more peptides belonging to the temporin and/or dermaseptin families.

BACKGROUND OF THE INVENTION

Plants are hosts to thousands of infectious diseases caused by a vast array of phytopathogenic fungi, bacteria, viruses, and nematodes. These pathogens are responsible for significant crop losses worldwide, resulting from both infection of growing plants and destruction of harvested crops. The most widely practiced methods of reducing the damage caused by such pathogens involve the use of various chemical agents. Unfortunately, many pathogens develop resistance to such chemicals, and some pathogens (especially viruses) are not susceptible to control by chemical means. In addition, many of the chemical agents used are broad-spectrum toxins, and may cause serious environmental damage, as well as toxicity in humans.

Plant breeding and, more recently, genetic engineering techniques have also been employed to combat plant pathogens. In certain instances, breeders and molecular biologists have successfully engineered resistance to certain pathogens. In the last few years, a number of plant R (resistance) genes have been isolated from plants. When introduced into otherwise susceptible crops, these R genes produce enhanced resistance to certain pathogens. For example, U.S. Pat. No. 5,571,706 describes the isolation of the tobacco N gene, which confers enhanced resistance to Tobacco Mosaic Virus. However, while conventional breeding and genetic engineering approaches reported to date can successfully enhance pathogen resistance, they typically address problems caused by just one pathogen, or a small number of closely related pathogens. As a result, while crops produced using these approaches may have enhanced protection against one pathogen, conventional chemical agents must still be used to control others.

It would be of great agricultural benefit to be able to produce plants having enhanced resistance to a broad spectrum of pathogens, including bacterial and fungal pathogens. It is to such plants that the present invention is directed.

SUMMARY OF THE INVENTION

The present inventors have discovered that the expression of certain peptides in transgenic plants confers broad spectrum pathogen resistance, including enhanced resistance to both fungal and bacterial pathogens. The peptides in question are small, positively charged (cationic) peptides belonging to the temporin and dermaseptin families, which occur naturally in the skin of certain species of frog. Transgenic plants provided by the invention may be used in conventional agricultural applications, such as food crops. Alternatively, the plants may be harvested and processed to extract the expressed temporin and/or dermaseptin peptides, which may then be purified for use in medical and other applications.

The invention thus encompasses transgenic plants that express at least one dermaseptin or temporin peptide, and methods of making such plants. Parts of such plants, including seeds, fruit, stems, leaves and roots, may be utilized in conventional ways as food sources, or as a source of the dermaseptin or temporin peptides. Because all plant types are susceptible to one or more plant pathogens, the present invention may be usefully applied to produce broad-spectrum resistance in any plant type. Thus, the invention may be applied to both monocotyledonous, dicotyledenous and gymnosperm plants, including, but not limited to maize, wheat, rice, barley, soybean, beans in general, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; and flowers such as orchids, carnations and roses.

In its most basic form, the invention provides transgenic plants that express one or more dermaseptin and/or temporin peptides. Members of the dermaseptin and temporin peptide families are well known in the art. Examples of dermaseptins that may be used in the invention include, but are not limited to, the dermaseptins described by Mor. et al., *Biochemistry*, 30:8824–8830, 1991, Strahilevitz, *Biochemistry*, 33:10951–10960, 1994 and Wechselberger, *Biochim. Biophys. Acta* 1388: 279–283, 1998. Examples of temporins that may be used include, but are not limited to, the temporins described by Simmaco et al., *Eur. J. Biochem.*, 242:788–92, 1996. In their natural state (i.e., expressed in frog cells), both dermaseptin and temporin peptides are produced as precursor forms that are subsequently processed by proteolytic cleavage to form mature proteins. The mature forms of dermaseptins are typically about 27–34 amino acids in length, while the mature forms of temporins are typically about 10–13 amino acids in length. The invention contemplates the use of both the naturally occurring full-length (unprocessed) forms of these peptides, as well as the mature (processed) forms of the peptides and intermediate forms. In addition, synthetic forms of the peptides may also be employed. Synthetic forms of the peptides include any form that is not naturally occurring, and encompasses peptides that differ in amino acid sequence from the naturally occurring peptides, but which still retain dermaseptin or temporin biological activity. Such sequence variants will typically retain at least 40% amino acid sequence identity with at least one naturally occurring dermaseptin or temporin peptide.

Other synthetic forms of dermaseptins and temporins that may be employed include forms having N-terminal peptide extensions. Such peptide extensions may comprise portions of the precursor forms of dermaseptins or temporins that are usually removed during protein processing, or may be synthetic sequences. These N-terminal peptide extensions may serve to provide enhanced resistance to proteolytic cleavage, and may also enhance the antimicrobial activity of the peptides. Typically, these N-terminal extensions are of between 2 and 25 amino acids in length, although longer extensions may also be employed. Examples of N-terminal extension sequences that are utilized in certain embodiments include the peptide sequences MAMWK (amino acids 1–5 of SEQ ID NO: 28) and MASRH (amino acids 1–5 of SEQ ID) NO: 34). The AMWK sequence (amino acids 1–5 of SEQ ID NO: 28) is a naturally-occurring peptide extension; it is part of the full-length dermaseptin-b peptide sequence that is normally cleaved during processing. The ASRH (amino acids 1–5 of SEQ ID NO: 34) is a synthetic extension sequence. In each case, the N-terminal methionine is added to the extension peptide to ensure proper expression of the peptide.

While the fundamental aspect of the invention is based on the expression of temporin and dermaseptin peptides in transgenic plants, other amino acid sequences may be joined to the peptides in order to produce fusion peptides. Expression of such fusion peptides in transgenic plants may provide even more effective broad-spectrum pathogen resistance than expression of temporin or dermaseptin peptides alone, r may enhance stability of the expressed dermaseptin/temporin molecule to provide higher expression levels, and thereby facilitate purification of the peptide from plant tissues. Thus, in other embodiments, the invention provides transgenic plants that express a fusion peptide comprising:

(1) a first peptide sequence that is a dermaseptin or a temporin; and (2) a second peptide sequence operably linked to the first peptide sequence.

The second peptide sequence is typically, but not necessarily, linked to the amino (N-) terminus of the first peptide sequence.

In certain embodiments, the second peptide sequence comprises an anionic (negatively charged) "pro-region" peptide sequence. Such pro-region peptides serve to neutralize the cationic nature of the dermaseptin or temporin and may thus provide enhanced stability in the cellular environment. Thus, these pro-regions generally include a number of negatively charged amino acids, such as glutamate (Glu or E) and aspartate (Asp or D). Suitable pro-regions include those that are found in naturally occurring unprocessed (full-length) dermaseptin and temporin peptides, as well as anionic pro-regions from other peptides, including those of mammalian origin, such as the pro-region from sheep cathelin proteins. Fusion peptides that include such pro-regions may be represented as P-D or P-T, wherein P is the pro-region peptide, T is a temporin peptide and D is a dermaseptin peptide.

Although such pro-region peptides may be directly joined to the N-terminus of the dermaseptin or temporin peptide, it may be beneficial to join the two peptides using a spacer peptide. The use of spacer peptides to join two peptide domains is well known in the art; such spacer peptides are typically of between 2 and 25 amino acids in length, and provide a flexible hinge connecting the first peptide sequence to the second peptide. Spacer sequences that have been used to provide flexible hinges connecting two peptide sequences include the glycine(4) serine spacer (GGGGS x3; SEQ ID NO: 42) described by Chaudhary et al., *Nature* 339: 394–397, 1989. Alternatively, an N-terminal peptide extension as described above may serve to provide the spacer peptide function. Fusion peptides that comprise a pro-region peptide, a spacer peptide and a dermaseptin or temporin peptide may be represented as P-S-D or P-S-T, wherein S represents the spacer peptide.

Spacer sequences may also include a cleavage site, such as a peptide sequence recognized and cleaved by a protease. Such sites facilitate removal of the pro-region from the dermaseptin or temporin peptide following purification from plant tissues.

These and other aspects of the invention are described in more detail in the following sections.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID: 1 shows the dermaseptin b cDNA sequence.

SEQ ID: 2 shows the amino acid sequence of the precursor (unprocessed) dermaseptin b peptide.

SEQ ID: 3 shows the 27 amino acid sequence of the mature dermaseptin b peptide.

SEQ ID: 4 shows the 31 amino acid sequence of the mature dermaseptin B peptide.

SEQ IDs: 5–14 show the amino acid sequences of various mature (processed) dermaseptin peptides.

SEQ ID: 15 shows a cDNA sequence encoding temporin G.

SEQ ID: 16 shows the amino acid sequence of the precursor (unprocessed) form of temporin G.

SEQ ID: 17 shows the 13 amino acid sequence of the mature temporin G peptide.

SEQ IDs: 18–26 show the amino acid sequences of various mature (processed) temporin peptides.

SEQ ID: 27 shows the nucleic acid sequence encoding $MSRA_2$.

SEQ ID: 28 shows the amino acid sequence of $MSRA_2$.

SEQ IDs: 29–32 show the oligos used to generate the nucleic acid sequence encoding $MSRA_2$.

SEQ IDs: 33 shows the nucleic acid sequence encoding $MSRA_3$.

SEQ ID: 34 shows the amino acid sequence of $MSRA_3$.

SEQ IDs: 35–38 show the oligos used to generate the nucleic acid sequence encoding $MSRA_3$.

SEQ IDs: 39–41 show the amino acid sequences of various N-terminal extension sequences.

SEQ ID NO: 42 shows the protein sequence of a glycine serine spacer (GGGGS x3).

I. DEFINITIONS

Figure 1:
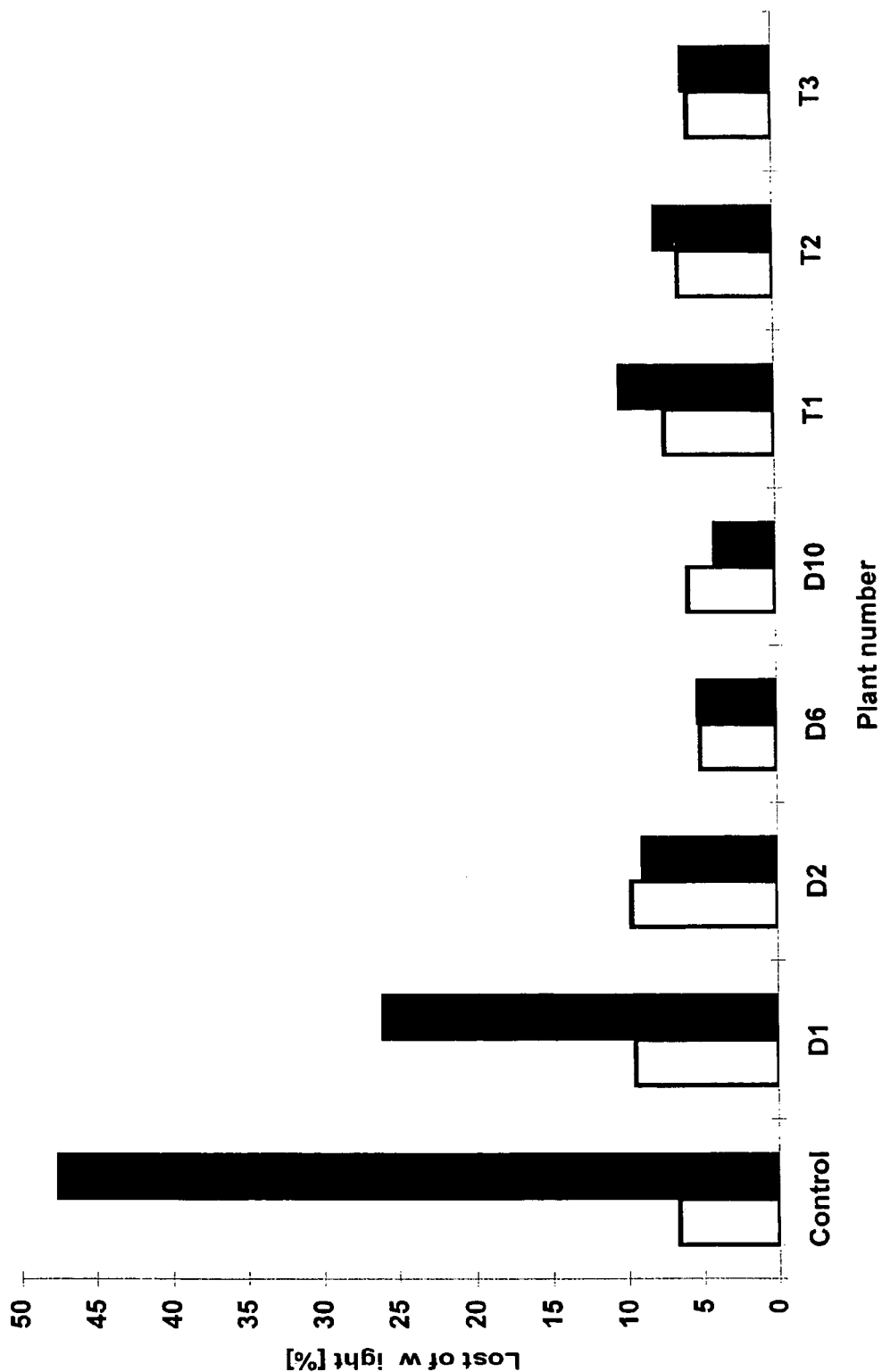
FIG. 1 is a graph that shows the results from assays that tested the resistance of transgenic potato tubers to soft rot. Discs prepared from tubers of Desiree control and transgenic plants expressing Demaseptin B (sample Nos. D1, D2, D6, D10) or Temporin A (sample Nos. T1, T2, T3) were infected with *E. carotovora* (black boxes) or left uninfected (white boxes). After 6 days at room temperature, rotted tissue was gently removed from the discs and the sensitivity/resistance to *E. carotovora* was expressed as the loss of weight of tuber tissue.

Dermaseptin: As used herein, the term "dermaseptin" refers to any member of the family of naturally occurring cationic peptides termed dermaseptins, (Strahilevitz, *Biochemistry*, 33:10951–960, 1994) as well as fragments and variants of these naturally occurring peptides that display dermaseptin biological activity as defined below.

Dermaseptins were first identified in skin extracts from the South American arboreal frog *Phyllomedusa sauvagii* (Mor et al., *J. Biol. Chem.*, 269: 31635–31641, 1994). They are broad-spectrum microbiocidal peptides that inhibit growth of filamentous fungi as well as bacteria, yeast, and protozoa (Strahilevitz, *Biochemistry*, 33:10951–10960, 1994). Since the first dermaseptin, dermaseptin S, was identified, a number of other members of this peptide family have been characterized and cloned, including: dermaseptin-b, isolated from the skin of *Phyllomedusa bicolor* (Mor et al., *J. Biol. Chem.*, 269: 31635–31641, 1994). (SEQ ID: 2); two dermaseptins isolated from *Pachymedusa dacnicolor*, and encoded by clones PD-3-3 and PD-2-2, as described by Wechselberger, *Biochim. Biophys. Acta* 1388:279–283, 1998 (the peptide sequences of which are shown in SEQ IDs: 5–6, respectively); three dermaseptins isolated from *Agalychnis annae* and encoded by clones AA-3-6, AA-3-3, AA-3-1, as described by Wechselberger, *Biochim. Biophys. Acta* 1388:279–283, 1998 (the peptide sequences of which are shown in SEQ IDs: 7–9, respectively); and five dermaseptin peptides from *Phyllomedusa sauvagii*, termed dermaseptin 5, dermaseptin 4, dermaseptin 3, dermaseptin 2, and dermaseptin 1, as described by Mor and Nicolas, *Journal Biochemical Chemistry*, 269:1934–1939, 1994 (the peptide sequences of which are provided in SEQ IDs: 10–14, respectively). These sequences are readily available from public databases, including from GenBank.

Dermaseptin peptides are typically expressed as precursor forms of around 60–80 amino acids in length, and are subsequently processed to mature forms of around 27–34 amino acids in length. For example, the cDNA encoding dermaseptin-b (SEQ ID:1; Amiche et al., *J. Biol. Chem.* 269:1747–1852, 1994; Chapentier et al., *Biol. Chem.* 273: 14690–14697, 1998; located in the GenBank nucleotide sequence database under accession number X72387) encodes a precursor peptide of 78 amino acids in length (SEQ ID: 2). This precursor form of dermaseptin-b is processed to produce two mature forms, termed dermaseptin b and dermaseptin B (Strahilevitz, *Biochemistry*, 33:10951–10960, 1994). Dermaseptin b (SEQ ID: 3) is 27 amino acids in length and comprises amino acid residues 49–75 of the precursor form. Dermaseptin B is an alternative cleavage product of 31 amino acids in length, and includes an N terminal extension of 4 amino acids (AMWK) (SEQ ID: 4). Dermaseptin B comprises amino acid residue 45–75 of the precursor form. With the exception of SEQ IDs: 1 and 2 which show the full-length precursor form of dermaseptin b, the dermaseptin peptides shown in the Sequence Listing represent the processed, mature forms of the peptides.

Given the availability of a wide range of dermaseptin peptide sequences, and the nucleic acid sequences that encode these peptides, one of ordinary skill in the art will readily be able to produce these peptides, and their corresponding nucleic acid sequences, using standard molecular biology techniques.

In addition to the use of the naturally occurring dermaseptin peptides described above, it will be apparent to one of skill in the art that the invention may be practiced using peptides that vary somewhat from the naturally occurring dermaseptin peptides, yet which nevertheless confer enhanced broad spectrum pathogen resistance when expressed in plants. For example, the N-terminal ∀-helical amphipathic segment of the mature dermaseptin peptides, particularly the first 18 amino acid residues, has been identified as important for antimicrobial activity (Mor et al., *J. Biol. Chem.*, 269:31635–31641, 1994; Mor and Nicolas, *Journal Biochemical Chemistry*, 269:1934–39, 1994) and this fragment may be used in place of the full-length mature dermaseptin. Thus, the term "dermaseptin" also encompasses variant dermaseptin peptides, as well as fragments of the naturally occurring peptides, that share a specified level of sequence identity with a naturally occurring dermaseptin peptide, or that differ from a naturally occurring dermaseptin peptide by one or more conservative amino acid substitutions.

Such variant peptides and fragments retain dermaseptin biological activity, which may be assayed by the methods described below. A variant dermaseptin will typically share at least 40% amino acid sequence identity with a naturally occurring dermaseptin peptide (such as the one shown in SEQ ID: 3) as determined by the methods described below.

Dermaseptin biological activity: the ability of a dermaseptin peptide to inhibit bacterial growth and/or fungal growth. Dermaseptin biological activity can readily be ascertained by using the protocols given below.

The antibacterial activity of a given dermaseptin peptide is assessed by determining its ability to inhibit the growth of a pectinolytic bacterial strain such as *Erwinia carotovora* or *Escherichia coli* DH5∀. The activity of a given peptide is determined by serially diluting the peptide in LB and aliquoting 100:1 to wells in a 96 well microtiter plate. A fresh bacterial culture (~0.3 A550) is then grown on Luria-Bertani medium (LB) (1% w/v tryptone and 0.5% w/v yeast extract) and diluted to $10^{-2}$ in LB to represent approximately $10^4$–$10^5$ colony forming units (CFU) ml$^{-1}$. 10:1 of the bacterial culture is then inoculated into the wells containing the peptide and the samples are incubated at 37° C. for 4 hours. The well contents are then diluted in LB, plated on LB agar and incubated overnight at 37° C. The colonies on plates corresponding to each dilution of dermaseptin (and a control to which no peptide was added) are then counted, and the antibacterial activity of the peptide under test is determined by comparison to the control plate.

The dermaseptin peptide is determined to have biological activity if, under the conditions of this assay, it is capable of inhibiting bacterial growth by at least 10% at a concentration of 7 μg per ml (i.e., at this concentration, the number of bacterial colonies is no more than 90% that of the control plate).

The antifungal activity of a given dermaseptin peptide is assessed by utilizing the fungal strains *Phytophthora cactorum* and/or *Fusarium solani*. The selected fungal strain is grown on Five Cereal Agar (FCA containing 20 gL$^{-1}$ five cereal baby food instant flakes, and 8 gL$^{-1}$ agar$^3$ (Terras et al., *The Plant Cell* 7:573–588, 1995). After 5 days growth at room temperature a mycelial plug is removed and placed upside down in the center of a fresh FCA plate. A sterile solution (10 μl) of the test peptide is then introduced into a well 3 cm from the edge of the plate and a control well containing sterile water is established on the same plate. Various concentrations of the test peptide may be tested on the same plate, or on other plates. The assay plates are incubated for 5 days at room temperature, after which the zone of growth inhibition around each well is measured.

The dermaseptin peptide is determined to have biological activity if, under the conditions of this assay, it is capable of inhibiting fungal growth at a concentration of 5 µg per ml (i.e., there is a discernible zone of inhibition around a well containing this concentration of peptide).

Temporin: As used herein, the term "temporin" refers to any member of the family of naturally occurring cationic peptides termed temporins (Simmaco et al., *Eur. J. Biochem.*, 242:788–92. 1996) as well as fragments and variants of these naturally occurring peptides that display temporin biological activity as defined below.

Temporins are small cationic peptides with anti-microbial activity that were initially identified from a cDNA library prepared from the skin of the frog, *Rana temporaria*. These peptides show some sequence similarity to hemolytic peptides isolated from *Vespa venom*, however, the temporin peptides are not hemolytic (Simmaco et al., *Eur. J. Biochem.*, 242:788–92.1996).

Ten members of the temporin family, temporins A, B, C, D, E, F, G, H, K, and L, have been described by Simmaco et al., *Eur. J. Biochem.*, 242:788–92. 1996. Like dermaseptins, temporins are typically expressed in a precursor form and subsequently processed to produce a mature form. For example, the cDNA molecule that encodes temporin G (shown in SEQ ID: 15, and located in the GenBank nucleotide database under accession number Y09395) encodes a 61 amino acid precursor form of temporin G (shown in SEQ ID: 16). Amino acids 1–22 comprise a signal sequence, amino acids 23–46 comprise a pro-region, and amino acids 47–59 comprise the processed, mature temporin G peptide (the mature form is shown in SEQ ID: 17). In general, the predicted mature temporin peptides are between 10 and 13 amino acids long, and some have been found to be amidated at the C-terminus (Simmaco et al., *Eur. J. Biochem.*, 242: 788–92. 1996). The mature forms of temporins A, B, C, D, E, F, G, H, K, and L are shown in SEQ IDs: 18, 19, 20, 21, 22, 23, 17, 24, 25, and 26, respectively.

Given the availability of a wide range of temporin peptide sequences, and the nucleic acid sequences that encode these peptides, one of ordinary skill in the art will readily be able to produce these peptides, and their corresponding nucleic acid sequences, using standard molecular biology techniques.

In addition to the use of the naturally occurring temporin peptides described above, it will be apparent to one of skill in the art that the invention may be practiced using peptides that vary somewhat from the naturally occurring temporin peptides, yet which nevertheless confer enhanced broad spectrum pathogen resistance when expressed in plants. Thus, the term "temporin" also encompasses variant temporin peptides, as well as fragments of the naturally occurring peptides, that share a specified level of sequence identity with a naturally occurring temporin peptide, or that differ from a naturally occurring temporin peptide by one or more conservative amino acid substitutions.

Such variant peptides and fragments retain temporin biological activity, which may be assayed by the methods described below. A variant temporin will typically share at least 40% amino acid sequence identity with a naturally occurring temporin peptide (such as the one shown in SEQ ID: 17) as determined by the methods described below.

Temporin biological activity: the ability of a temporin peptide to inhibit bacterial growth.

The antibacterial activity of a given temporin peptide is assessed by determining its ability to inhibit the growth of a pectinolytic bacterial strain such as *Erwinia carotovora* or *Escherichia coli* DH5∀. The activity of a given peptide is determined by serially diluting the peptide in LB and aliquoting 100:1 to wells in a 96 well microtiter plate. A fresh bacterial culture (~0.3 A550) is then grown on Luria-Bertani medium (LB) (1% w/v tryptone and 0.5% w/v yeast extract) and diluted to $10^{-2}$ in LB to represent approximately $10^4$–$10^5$ colony forming units (CFU) $ml^{-1}$. 10:1 of the bacterial culture is then inoculated into the wells containing the peptide and the samples, are incubated at 37° C. for 4 hours. The well contents are then diluted in LB, plated on LB agar and incubated overnight at 37° C. The colonies on plates corresponding to each dilution of temporin (and a control to which no peptide was added) are then counted, and the antibacterial activity of the peptide under test is determined by comparison to the control plate.

The temporin peptide is determined to have biological activity if, under the conditions of this assay, it is capable of inhibiting bacterial growth by at least 10% at a concentration of 100 µg per ml (i.e., at this concentration, the number of bacterial colonies is no more than 90% that of the control plate).

The antifungal activity of a given temporin peptide is assessed by utilizing the fungal strains *Phytophthora caclorum* and/or *Fusarium solani*. The selected fungal strain is grown on Five Cereal Agar (FCA containing 20 $\mu L^{-1}$ five cereal baby food instant flakes, and 8 $gL^{-1}$ agar$^3$ (Terras et al., *The Plant Cell*, 7:573–588, 1995). After 5 days growth at room temperature a mycelial plug is removed and placed upside down in the center of a fresh FCA plate. A sterile solution (10:1) of the test peptide is then introduced into a well 3 cm from the edge of the plate and a control well containing sterile water is established on the same plate. Various concentrations of the test peptide may be tested on the same plate, or on other plates. The assay plates incubated for 5 days at room temperature, after which the zone of growth inhibition around each well is measured.

The temporin peptide is determined to have biological activity if, under the conditions of this assay, it is capable of inhibiting fungal growth at a concentration of 5 µg per ml (i.e., there is a discernible zone of inhibition around a well containing this concentration of peptide).

Transgenic plant: As used herein, this term refers to a plant that contains recombinant genetic material not normally found in a wild-type plant of this species. Thus, a plant that is grown from a plant cell into which recombinant DNA is introduced by transformation is a transgenic plant, as are all offspring of that plant that contain the introduced transgene (whether produced sexually or asexually).

Sequence identity: The similarity between two nucleic acid sequences, or two amino acid sequences is expressed in terms of the level of sequence identity shared between the sequences. Sequence identity is typically expressed in terms of percentage identity; the higher the percentage, the more similar the two sequences are.

Methods of alignment of sequences for comparison are well known in the art. Various programs and alignment algorithms are described in: Smith and Waterman, *Adv. Appl. Math*, 2:482, 1981; Needleman and Wunsch, *J. Mol. Biol.*, 48:443, 1970; Pearson and Lipman, *Proc. Natl. Acad. Sci. USA*, 85:2444, 1988; Higgins & Sharp, *Gene*, 73:237–244, 1988; Higgins & Sharp, *CABIOS*, 5:151–153, 1989; Corpet et al., *Nucleic Acids Research*, 16:10881–10890, 1988;

Huang, et al., *Computer Applications in the Biosciences,* 8:155–165, 1992; and Pearson et al., *Methods in Molecular Biology,* 24:307–331, 1994. Altschul et al., *Nature Gene* 6:119–129, 1994 presents a detailed consideration of sequence alignment methods and homology calculations.

The NCBI Basic Local Alignment Search Tool (BLAST) (Altschul et al., *J. Mol. Biol.* 215:403–410, 1990) is available from several sources, including the National Center for Biotechnology Information (NCBI, Bethesda, MD) and on the Internet, for use in connection with the sequence analysis programs blastp, blastn, blastx, tblastn and tblastx.

Variants of naturally occurring dermaseptin and temporin peptides useful in the present invention are typically characterized by possession of at least 40% sequence identity counted over the full-length alignment with the amino acid sequence of a naturally occurring temporin or dermaseptin peptide when aligned using the NCBI Blast 2.0.1 (described in Altschul et al., *Nucleic Acids Res.* 25:3389–3402, 1997). For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 70%, at least 80%, at least 85%, at least 90%, or at least 95% sequence identity.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Oligonucleotide (oligo): A linear polynucleotide sequence of up to about 100 nucleotide bases in length.

Probes and primers: Nucleic acid probes and primers may readily be prepared based on the amino acid sequence provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., *Molecular Cloning: A Laboratory Manual,* Cold Spring Harbor, 1989 and Ausubel et al., *Current Protocols in Molecular Biology,* Greene Publishing Associates and Wiley-Intersciences, 1987.

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al., *Molecular Cloning: A Laboratory Manual,* Cold Spring Harbor, 1989; Ausubel et al., *Current Protocals in Molecular Biology,* Greene Publishing Associates and Wiley-Intersciences, 1987; and Innis et al., *PCR Protocols, A Guide to Methods and Applications,* 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. Two peptide sequences may be operably linked through a normal peptide bond, or by other covalent linkage.

II. Selection of Dermaseptin and Temporin Peptides a. Dermaseptin Peptides

A listing of exemplary dermaseptin peptides is provided above. Nucleic acid molecules encoding these dermaseptin polypeptides may either be derived by simple application of the genetic code to the peptide sequence, or the naturally occurring cDNA or gene sequence may be employed. For example, a cDNA sequence encoding dermaseptin-b is provided in SEQ ID: 1 (and disclosed in Amiche et al., *J. Biol. Chem.* 269: 1747–852, 1994). Typically, the mature form of the dermaseptin peptide will be selected for expression. However, any fragment of a full-length dermaseptin peptide may be selected, contingent upon that fragment having dermaseptin biological activity if it is to be used to produce pathogen-resisting plants.

One of ordinary skill in the art will appreciate that the various dermaseptin peptides have varying degrees of antimicrobial activity, with some working more effectively against certain pathogens then others. Therefore, when selecting peptides for producing transgenic plants with enhanced pathogen resistance, the selection of a particular dermaseptin will be depend upon, among other factors, the type of plant in which the peptide is to be expressed, and the types of pathogens that commonly infect that plant type.

Having selected the desired dermaseptin peptide to be expressed, a nucleic acid molecule encoding the peptide may be produced by standard molecular biology techniques. Because the dermaseptin peptides are relatively short, the simplest way to synthesize the nucleic acid molecule will likely be via synthesis of overlapping oligonucleotides on a commercially available oligonucleotide synthesizer. The oligonucleotides can then be assembled into a full-length coding region in vitro. This approach also permits the selection of codons encoding particular amino acid residues that reflect the codon usage bias of the plant into which the nucleic acid molecule is to be introduced, thereby enhancing the expression efficiency. Detailed examples of the production of coding sequences using this approach are provided in the examples below.

b. Temporin Peptides

A listing of exemplary temporin peptides is provided above. Nucleic acid molecules encoding these temporin peptides may either be derived by simple application of the genetic code to the peptide sequence, or the naturally occurring cDNA or gene sequence may be employed. For example, the cDNA sequence encoding temporin G is provided in SEQ ID: 15. Typically, the mature form of the temporin peptide will be selected for expression. However, any fragment of a full-length temporin peptide may be selected, contingent upon that fragment having dermaseptin biological activity if it is to be used to produce pathogen-resisting plants.

As with the selection of dermaseptin peptides, one of ordinary skill in the art will appreciate that the various temporin peptides have varying degrees of anti-microbial activity, with some working more effectively against certain pathogens then others. Therefore, when selecting peptides for producing transgenic plants with enhanced pathogen resistance, the selection of a particular temporin will be depend upon, among other factors, the type of plant in which the peptide is to be expressed, and the types of pathogens that cause losses in that plant type.

As described above for dermaseptins, the synthesis and assembly of overlapping oligonucleotides is a simple and convenient way to produce nucleic acid molecules that encode temporins.

c. Addition of Other Peptide Sequences

The temporin and dermaseptin proteins may be also expressed in transgenic plants in the form of fusion proteins. Although any desired peptide may be fused to the selected dermaseptin or temporin protein for expression in plants, the expression, of fusion proteins comprising an anionic pro-region peptide operably linked to the amino terminus of the dermaseptin or temporin is expected to be particularly beneficial. Any anionic pro-region peptide may be employed for this purpose, including the anionic pro-regions that are found in naturally occurring full-length (i.e., unprocessed) dermaseptin and temporin peptides. For example, the pro-region comprising amino acids 23–46 of temporin G (shown in SEQ ID: 16) may be used as a pro-region. Such pro-region peptides serve to neutralize the cationic nature of the dermaseptin or temporin and may thus provide enhanced stability in the cellular environment. Thus, these pro-regions generally include a number of negatively charged amino acids, such as glutamate (Glu or E) and aspartate (Asp or D).

Examples of other naturally occurring pro-region peptides that are known in the art include pro-region peptides of the following proteins: the human neutrophil defensin protein (Daher et al., *Proc. Natl. Acad. Sci USA*, 85:7327–7331, 1988); the bovine antimicrobial cathelicidin protein BMAP28 (Skerlavaj et al., *J. Biol. Chem.* 271: 28375–381, 1996); the sheep antimicrobial cathelin family of proteins (Mahoney et al., *FEBS Lett.* 377:519–522, 1995); bovine indolicidin (Del Sal et al., *Biochem. Biophys. Res. Commun.* 187:467–472, 1992); the porcine antimicrobial peptides prophenin-2 and PR-39 (Zhao et al., *FEBS Lett.* 367:130–134, 1995) and PMAP-37 (Tossi et al., *Eur. J. Biochem*, 15:941–946, 1995); the human antimicrobial lipopolysaccharide binding protein CAP18 (Larrick et al., *Infect. Immun.* 63:1291–1297, 1995); and the murine protein E3 (Scott and Collins, *Blood* 88:2517–2530, 1996).

While the anionic pro-region peptide may be directly joined to the N-terminus of the cationic peptide, an alternative embodiment involves linking the pro-region peptide to the dermaseptin or temporin peptide using a spacer peptide sequence. The use of spacer peptides to join two peptide domains is well known in the art; such spacer peptides are typically of between 2 and 25 amino acids in length, and provide a flexible hinge connecting the first peptide sequence to the second peptide. Spacer sequences that have been used to provide flexible hinges connecting two peptide sequences include the glycine(4)-serine spacer (GGGGS ×3; SEQ ID NO: 42) described by Chaudhary et al., *Nature* 339: 394–397, 1989. Alternatively, an N-terminal peptide extension as described below may serve to provide the spacer peptide function. Spacer sequence peptides may also include a cleavage site, such as a peptide sequence recognized and cleaved by a protease, such as Factor Xa. Such sites facilitate removal of the pro-region from the dermaseptin or temporin peptide following purification from plant tissues. The use of anionic pro-region peptides and spacer peptides to express certain cationic peptides in microbial systems is known in the art and described in U.S. Pat. No. 5,593,866 to Hancock.

In certain embodiments, an N-terminal extension peptide sequence may be added to the dermaseptin or temporin peptide. Such peptide extensions may comprise portions of the precursor forms of dermaseptins or temporins that are usually removed during protein processing, or may be synthetic sequences. These N-terminal peptide extensions may serve to provide enhanced resistance to proteolytic cleavage, enhance transcription levels, or enhance the anti-microbial activity of the peptides. Typically, these N-terminal extensions are of between 2 and 25 amino acids in length, although longer extensions may also be employed. Examples of N-terminal extension sequences that are utilized in certain embodiments include the peptide sequences AMWK (SEQ ID: 39), ASRH (amino acids 2–5 of SEQ ID NO: 34), and ALWK (SEQ ID NO: 41). The AMWK (SEQ ID: 39) sequence is a naturally-occurring peptide extension; it is part of the full-length dermaseptin-b peptide sequence that is normally cleaved during processing. The addition of this sequence to the N-terminus of dermaseptin b (to produce dermaseptin B) has been reported to enhance the in vitro antimicrobial activity of the peptide (Strahilevitz, *Biochemistry,* 33:10951–10960, 1995). The ASRH (SEQ ID: 40), and ALWK (SEQ ID: 41) peptides are synthetic extension sequence. In each case, an N-terminal methionine is added to ensure proper expression of the peptide. One of skill in the art will appreciate that the effect of adding any particular N-terminal extension peptide on the biological activity of the peptide being produced (dermaseptin or temporin) may readily be assessed using the biological activity assay described above.

d. Variant Dermaseptin and Temporin Peptides

As described above, a number of naturally occurring temporin and dermaseptin peptides are known, exemplified by those shown in the Sequence Listing. Variants on these naturally occurring peptides may be selected by introducing amino acid substitutions, additional amino acid residues, or by deleting amino acid residues. These variant peptides may either be produced by chemical synthesis (for example, in order to confirm that the variant peptide retains functional activity), or may be produced in a biological expression system. In the latter instance, the nucleic acid sequence encoding the corresponding naturally occurring peptide can be manipulated so that it encodes the variant peptide. This can be done through a variety of methods, for example by using site-directed mutagenesis or the polymerase chain reaction. Alternatively, because the peptides are relatively short molecules, the coding region for a variant peptide can simply be synthesized de novo and introduced into a suitable expression vector.

The simplest modifications of amino acid sequences involve the substitution of one or more amino acids for amino acids having similar biochemical properties. These so-called conservative substitutions are likely to have minimal impact on the activity of the resultant protein. Thus, peptides that differ from naturally occurring temporin or dermaseptin peptides by one or more conservative amino acid substitutions may be used in the invention in place of the naturally occurring peptides. Table 1 shows amino acids which may be substituted for an original amino acid in a protein and which are regarded as conservative substitutions.

TABLE 1

| Original Residue | Conservative Substitutions |
| --- | --- |
| Ala | ser |
| Arg | lys |
| Asn | gln; his |
| Asp | glu |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in functional or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. Variant peptides having one or more of these more substantial changes may also be employed in the invention, provided that temporin or dermaseptin biological activity is retained.

More extensive amino acid changes may also be engineered into variant dermaseptin or temporin peptides. As noted above however, these variant peptides will typically be characterized by possession of at least 40% sequence identity counted over the full-length alignment with the amino acid sequence of their respective naturally occurring sequences using the alignment programs described above. In addition, these variant peptides will retain biological activity.

Confirmation that a dermaseptin or temporin peptide has biological activity may be achieved using the assay systems described above. Following confirmation that the peptide has the desired activity, a nucleic acid molecule encoding the peptide may be readily produced using standard molecular biology techniques. Where appropriate, the selection of the open reading frame will take into account codon usage bias of the plant species in which the peptide is to be expressed.

III. Introducing Dermaseptins and/or Temporins inton Plants

Once a nucleic acid sequence encoding a dermaseptin and/or a temporin peptide has been produced, standard techniques may be used to express the sequence in transgenic plants in order to confer pathogen resistance to the plant. The basic approach is to clone the nucleic acid into a transformation vector, such that it is operably linked to control sequences (e.g., a promoter) that direct expression of the nucleic acid in plant cells. The transformation vector is then introduced into plant cells by one of a number of techniques (e.g., electroporation), whole plants are regenerated from the cells, and progeny plants containing the introduced nucleic acid are selected. Preferably all or part of the transformation vector will stably integrate into the genome of the plant cell. That part of the transformation vector which integrates into the plant cell and which contains the introduced sequence and associated sequences for controlling expression (the introduced "transgene") may be referred to as the recombinant expression cassette.

Selection of progeny plants containing the introduced transgene may be made based upon the detection of an altered phenotype. Such a phenotype may result directly from the disease resistance conferred by the introduced sequence or may be manifested as enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,510,471 ("Chimeric Gene for the Transformation of Plants")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5,750,871 ("Transformation and Foreign Gene Expression in Brassica Species")
U.S. Pat. No. 5,268,526 ("Overexpression of Phytochrome in Transgenic Plants")
U.S. Pat. No. 5,780,708 ("Fertile Transgenic Corn Plants")
U.S. Pat. No. 5,538,880 ("Method For Preparing Fertile Transgenic Corn Plants")
U.S. Pat. No. 5,773,269 ("Fertile Transgenic Oat Plants")
U.S. Pat. No. 5,736,369 ("Method For Producing Transgenic Cereal Plants")
U.S. Pat. No. 5,610,042 ("Methods For Stable Transformation of Wheat").

These examples include descriptions of transformation vector selection, transformation techniques and the construction of constructs designed to over-express the introduced transgene.

a. Plant Types

Diseases caused by many pathogens affect a wide variety of plant species. These plants can be monocots, dicots or gymnosperms. Thus, for example, dermaseptins and/or temporin peptides may be introduced into plant species including, but not limited to, maize, wheat, rice, barley, soybean, beans in general, rape/canola, alfalfa, flax, sunflower, safflower, brassica, cotton, tobacco, flax, peanut, clover, cowpea, grapes; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; fur trees such as Douglas fir and loblolly pine, and flowers such as carnations and roses.

b. Vector Construction and Choice of Promoters

A number of recombinant vectors suitable for stable transfection of plant cells or for the establishment of transgenic plants have been described including those described in Pouwels et al., *Cloning Vectors: A Laboratory Manual*, 1985, supp., 1987; Weissbach and Weissbach, *Methods for Plant Molecular Biology*, Academic Press, 5:173–184, 1989; and Gelvin et al., *Plant Molecular Biology Manual*, Kluwer Academic Publishers, 1990. Typically, plant transformation vectors include one or more cloned sequences under the transcriptional control of 5' and 3' regulatory sequences and a dominant selectable marker. Such plant transformation vectors typically also contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal. Examples of constitutive plant promoters that may be useful for expressing a transgene include: the cauliflower mosaic virus (CaMV) 35S promoter, which confers constitutive, high-level expression in most plant tissues (see e.g., Odel et al., *Nature*, 313:810, 1985; Dekeyser et al., *Plant Cell*, 2:591, 1990; Terada and Shimamoto, *Mol. Gen. Genet.* 220:389, 1990; and Benfey and Chua, *Science*, 250:959–966, 1990) the nopaline synthase promoter (An et al., *Plant Physiol.* 88:547, 1988); the octopine synihase promoter (Fromm et al., *Plant Cell*, 1:977, 1989) and the 2×CaMV/35S promoter with a translational enhancer sequence (Kay et al., *Science*, 236:1299–1302, 1987).

A variety of plant gene promoters that are regulated in response to environmental, hormonal, chemical, and/or developmental signals, also can be used for expression of a transgene in plant cells, including promoters regulated by: (a) heat (Callis et al., *Plant Physiol.*, 88:965, 1988; Ainley et al., *Plant Mol. Biol.*, 22:13–23, 1993; and Gilmartin et al., *The Plant Cell*, 4:839–949, 1992) (b) light (e.g., the pea rbcS-3A promoter, Kuhlemeier et al. *Plant Cell*, 1:471, 1989, and the maize rbcS promoter, Schaffner & Sheen, *Plant Cell*, 3:997, 1991); (c) hormones, such as abscisic acid (Marcotte et al., *Plant Cell*, 1: 471, 1989); (d) wounding (e.g., the potato PinII promoter (Keil et al., *Nucl. Acids. Res.* 14: 5641–5650, 1986), the *Agrobacterium* mas promoter (Langridge et al. *Bio/Technology* 10:305–308, 1989), and the grapevine vst1 promoter (Weise et al. *Plant Mol. Biol.*, 26:667–677, 1994); and (e) chemicals such as methyl jasmonate or salicylic acid (see also Gatz et al. *Plant Mol. Biol.* 48:89–108, 1997).

Alternatively, tissue specific (root, leaf, flower, and seed for example) promoters (Carpenter et al., *The Plant Cell* 4:557–571, 1992; Denis et al., *Plant Physiol.* 101: 1295–1304, 1993; Opperman et al., *Science* 263:221–223, 1993; Stockhause et al., *The Plant Cell* 9:479–489, 1997; Roshal et al., *The EMBO J.* 6:1155, 1987; Schemthaner et al., *EMBO J.* 7:1249, 1988; Yamamoto et al., *Plant Cell* 3:371–382, 1990; and Bustos et al., *Plant Cell* 1:839, 1989) can be fused to the coding sequence to obtain particular expression in respective organs.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Transformation and Regeneration Techniques

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobaclerium tumefaciens* (AT) mediated transformation. Typical procedures for transforming and regenerating plants are described in the patent documents listed at the beginning of this section.

d. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

Selection can also be accomplished by exploiting the pathogen resistance that is conferred to the plant via the transgene. As described in the Examples below, such screening may be accomplished either after the transgenic plants have been regenerated, or (depending on the transformation method used) may be performed on green transgenic callus prior to plant regeneration.

IV. Plants Containing Coding Regions for Multiple Cationic Peptides

In some cases, the level of resistance that is conferred by a single copy of a transgene encoding a dermaseptin or a temporin peptide may be enhanced by introducing multiple copies of a single cationic peptide gene, or several genes encoding different cationic peptides.

Through the use of genetic engineering it is possible to introduce coding regions for multiple cationic peptides into a single vector. Typically (though not necessarily) such vectors comprise two or more dermaseptin and/or temporin open reading frames each operably linked to its own 5' and 3' regulatory sequences. When introduced into plants, such vectors can result in the expression of multiple varieties of cationic peptides.

The creation of a plant containing multiple transgenes can also be accomplished through the use of standard breeding techniques. A transgene encoding a first cationic peptide can be introduced into a first plant and a second transgene encoding a second cationic peptide can be introduced into a second plant. The resulting transgenic plants can then be crossed to produce progeny that carry both transgenes.

V. Production and Isolation of Dermaseptins and Temporins

The compositions and methods described above may be used not only to produce plants having enhanced, broad spectrum pathogen resistance, but may also be used for the large scale production of dermaseptins and temporins for a wide range of other applications. For example, temporins and dermaseptins produced in large quantities in plants may be purified and used in medical applications.

The production of biologically active peptides in plants is now widely practiced, and bulk expression and purification methods are well known. Examples of constructs that facilitate the production of biologically active proteins in plants can be found in U.S. Pat. No. 4,956,282 to Goodman et al. These constructs generally contain a promoter region and an additional nucleic acid sequence that encodes an amino acid sequence that is later utilized in the purification process. The amino acid sequence that is used to facilitate the isolation of the dermaseptin and/or temporin peptides can be subsequently cleaved and discarded.

EXAMPLES

1. Selection and Creation of Nucleic Acid Sequences Encoding the Dermaseptin and the Temporin Peptides a. Dermaseptin Coding Sequence A nucleic acid molecule was designed to encode the mature 27 amino acid form of dermaseptin b (SEQ ID: 3) with a 5 amino acid N-terminal extension sequence, MAMWK (amino acids 1–5 of SEQ ID NO: 28). This nucleic acid construct was designated $MSRA_2$ and was synthesized using four overlapping oligonucleotides in a single PCR reaction. The oligonucleotides used are shown in Table 2. The first two oligonucleotides (oligo #1 and oligo #2) contained the nucleic acid sequences encoding the N-terminal and the C-terminal portions of the peptide, respectively. These oligonucleotides were used in the PCR reaction at a 20 nM concentration. The second two oligonucleotides contained sequences recognized by various restriction enzymes. Specifically, oligo #3 contained restriction sites for XbaI, KpnI and NcoI, and oligo #4 contained restriction site for SstI, PstI and HindIII. These oligonucleotides were used at a concentration of 200 nM in the PCR reaction. Following amplification of the product, it was cloned using the built-in restriction sites into a conventional cloning vector. The nucleic acid sequence of the coding region of $MSRA_2$ is shown in SEQ ID: 27, and the encoded peptide is shown in SEQ ID: 28. Oligo #s 1–4 are shown in SEQ IDs: 29–32.

TABLE 2

```
Oligo #1: 5'-ATGGCCATGTGGAAAGACGTT CTG AAA AAG         (SEQ ID:29)
             ATC GGT ACT GTC GCC CTC CAT GCA GGG-3'

Oligo #2: 3'-TGA CAG CGG GAG GTA CGT CCC TTC CGG CGC   (SEQ ID:30)
             GAA CCT CGT CAT CGGCTGTGGTAGAGCGTCATT-5'

Oligo #3: 5'-TCT AGA GGT ACC ATGGCCATGTGGAAAGACG-3'    (SEQ ID:31)

Oligo #4: 3'-GGCTGTGGTAGAGCGTCATTC TCG AGA CGT CTT    (SEQ ID:32)
             CGA AC-5'
```

The nucleotides in bold represent the regions of complementarity between oligo #1 and oligo #2.
The underlined portion of oligo #1 is identical to underlined portion of oligo #3, thus allowing oligo #3 to bind to the PCR product from the initial elongation of oligos #1 and #2. Similarly, the underlined portions of oligo #4 are identical to the underlined portion of oligo #2. This allows oligo #4 to bind to the PCR product created by elongation of oligos #1 and #2.

b. Temporin Coding Sequence

A nucleic acid molecule was designed to encode the mature 13 amino acid form of temporin A (SEQ ID:33) with a 6 amino acid N-terminal extension sequence, MASRHM (amino acids 1–6 of SEQ ID NO: 34). This nucleic acid construct was designated $MSRA_3$ and was synthesized using four overlapping oligonucleotides in a single PCR reaction. The oligonucleotides used are shown in Table 3. The first two oligonucleotides (oligo #1 and oligo #2) contained the nucleic acid sequences encoding the prototype peptide. However, unlike the oligonucleotides used to encode the prototype dermaseptin peptide, these oligonucleotides were fully complementary, thus eliminating the need for an initial elongation cycle prior to the binding of oligos #3 and #4.

Oligos #1 and #2 were used in the PCR reaction at a 20 nM concentration. The second two oligonucleotides contained sequences recognized by various restriction enzymes. Specifically, oligo #3 contained restriction sites for XbaI, KpnI and NdeI, and oligo #4 contained restriction site for SstI, and PstI. These oligonucleotides were used at a concentration of 200 nM in the PCR reaction.

Following amplification of the product, it was cloned using the built-in restriction sites into a conventional cloning vector. The nucleic acid sequence of the coding region of MSRA$_3$ is shown in SEQ ID:33, and the encoded peptide is shown in SEQ ID: 34. Oligo #s 1–4 are shown in SEQ IDs: 35–38.

TABLE 3

```
Oligo #1: 5'-ATG TTT CTG CCC CTA ATC GGG AGG GTT CTC TCG    (SEQ ID:35)
             GGA ATC CTG TAA-3'

Oligo #2: 3'-TAC AAA GAC GGG GATTAG CCC TCC CAA GAG         (SEQ ID:36)
             AGC CCT TAG GAC ATT-5'

Oligo #3: 5'-GGT ACC TCT AGA CAT ATG TTT CTG CCC CTA-3'     (SEQ ID:37)

Oligo #4: 3'-GAG AGC CCT TAG GAG ATTCTC GAG ACG TC-5'       (SEQ ID:38)
```

The nucleotides in bold represent the regions of complementarity between oligo #1 and oligo #2. As depicted in the diagram these sequences are fully complementary.
The underlined portions oligo #2 are complementary to the underlined portions of oligo #3 and the underlined portions of oligo #1 are complementary to the underlined portions of oligo #4.

The resulting double stranded DNA was then cloned into one or more of the vectors described below.

2. Vectors Containing Various Promoter Sequences

The nucleic acid sequences encoding MRSA$_2$ and MRSA$_3$ were assembled into various plant transformation vectors, thereby placing them under the transcriptional control of a variety of different promoters.

Cloning $MRSA_2$ and $MRSA_3$ sequences into one such vector placed the respective sequences under the control of a promoter that contained two copies of the CAMV 35S promoter and an AMV RNA4 translation enhancing element (Kay et al., *Science* 236:1299–1302, 1987). The clones that resulted from ligation into this vector were given the prefix pD as a designation. Therefore, $pDMSRA_2$ designates a vector which contains the $MSRA_2$ construct under the control of the double CaMV 35S promoter and the AMV RNA4 translational enhancer. Similarly, $pDMSRA_3$ designates a vector that contains the $MSRA_3$ construct under the control of the double CaMV 35S promoter with the AMV RNA4 translational enhancer.

Another vector was designed such that the $MSRA_2$ construct was under the control of a rebuilt "super promoter". This promoter contained the mas (mannopine synthase) promoter/activator region (Langridge et al., *Bio/Technology* 10:305–308, 1989) preceded by a timer of ocs (octopine synthase) upstream activating sequence (in inverted orientation). A more detailed description of this super promoter is provided in Ni et al., *The Plant J.,* 7:661–676, 1995. This particular construct also contained a coding region for a 6×His tag, positioned upstream of and operably linked to the $MSRA_2$ coding region. The 6×His tag amino acid sequence is thus expressed as an N-terminal addition to the encoded dennaseptin/MAMWK (SEQ ID NO:28) peptide. The vector encoding this peptide was designated $pRSHMSRA_2$.

3. Transformation of Potato and Tobacco

Potato cultivars, Russert Burbank and Desiree, as well as tobacco were used as representative plant species for transformation. The transformation of the plants was performed according to DeBlock, *Theoret. Appl. Genet.* 76:767–774, 1988, with some modifications.

Briefly, transformations of tobacco and potato were carried out by isolating leaves (5 mm) and stems from 4-week-old shoots. These leaves and shoots were cut and further wounded by scratching with glass pipette tips. Wounded leaves and stems were then floated upside down on 15 ml of S2 medium in a petri dish. This medium contained the components listed in Murashige and Skoog, *Physiol. Plant.* 15:473–479, 1962, supplemented with 30 g/L sucrose 0.5 g/L MES, pH 5.5, and 20 g/L mannitol.

60 µl of LB medium containing *Agrobacterium* (transformed with the vector of interest) in the late log phase of growth was added to each petri dish, and the dishes were then incubated at low light intensity (500 lux) for 3 days in the presence of the *Agrobacterium*. The plant tissue was then washed with S2 medium containing 1 g/L carbenicillin, blotted dry on filter paper, and placed upside down on S4 medium. S4 medium contained the components listed in Murashige and Skoog, *Physiol. Plant.* 15:473–479, 1962 minus sucrose and supplemented with 200 mg/L glutamine, 0.5 g/L MES, pH 5.7, 0.5 g/L PVP, 20 g/L mannitol, 20 g/L glucose, 40 mg/L adenine-$SO_4$, 0.5% agarose, 1 mg/L trans-zeatin, 0.1 mg/L NAA, 1 g/L carbenicillin and 50 µg/ml kanamycin, 10 mg/L $AgNO_3$). The plant tissue samples were placed at room temperature (RT) at 3000 lux to allow for callus formation. After two weeks, many small calli formed at the wounded edges of the leaves and stems. The small calli were removed and transferred to fresh S6 medium (S4 without NAA). After 2–3 weeks, the calli were transferred to S8 medium (S6 supplemented with 0.1 mg/L $GA_3$) to allow for shoot formation.

After two weeks on S8 medium, the first shoots (0.5 cm) were transferred to S1 medium. This medium contained the components described in Gamborg et al., *Exp. Cell Res.* 50:151–158, 1968, with the addition of 20 g/L sucrose, 150 mg/L $CaCl_2$, 0.4% agarose, pH 5.8, 1 g/L carbenicillin and 50 µg/ml kanamycin. The S1 medium and the shoots were placed in Magenta jars to allow for root formation. After one week the shoots had rooted. In order to avoid selecting identical shoots, transfer of shoots from the same or closely linked calli was avoided.

The regenerated putative transgenic plants were transferred to MS medium containing 1 g/L carbenicillin and 50 µg/ml kanamycin for further analysis.

4. Screening of Calli for Disease Resistance

A simplified early detection method for disease resistance assays was developed. Control and transgenic calli were grown on S4 medium (MS media without sucrose and supplemented with 200 mg/L glutamine, 0.5 g/L MES, pH 5.7, 0.5 g/L PVP, 20 g/L mannitol, 20 g/L glucose, 40 mg/L adenine-SO4, 0.5% agarose, 1 mg/L trans-zeatin, 0.1 mg/L NAA, 1 g/L carbenicillin and 50 µg/ml kanamycin, 10 mg/L AgNO3). The samples were then placed at RT at 3000 lux to allow for callus formation. After two weeks, many small calli formed at wounded edges of the leaves and stems. The small calli were removed and transferred to fresh S6 medium (S4 without NAA). After 2–3 weeks, the calli were transferred to fresh medium and grown in the presence of phytopathogens, *Fusarium* or *Phytophthora*. At the end of the expenments, calli that survived and stayed bright green were scored. No fungal resistant calli were found in the control samples, and calli that were resistant to the fungal pathogen were found to be transformed.

5. Molecular Characterization of Transgenic Plants

DNA was isolated from the transgenic potato and tobacco plants using the methods described below. In some instances purification involved a more rigorous protocol and in others a simple crude extract procedure was performed. The more rigorous extract procedure started by obtaining ten grams of fresh leaf tissue, and immediately freezing the sample in liquid nitrogen. The frozen tissue was then ground into a fine power and extracted with 20 ml extraction buffer (50 mM Tris-HCl buffer, 5 mM EDTA, 0.35 M sorbitol, 0.1% BSA, 0.1% β mercaptoethanol, 10% PEG 4000). The homogenate was filtered through several layers of cheesecloth and one layer of miracloth. The final purification steps were then performed in accordance with Wagner et al., *Proc. Natl. Acad. Sci. U.S.A.* 84:2097–5100, 1987.

The crude extract procedure was used mainly when isolation was being done for the purposes of PCR analysis. For this procedure about 200 mg of fresh leaves were collected and ground in liquid nitrogen into a powder. 100 µl of 0.5 N NaOH was added to the powder and mixed (vortexed) for 30 seconds. The suspension was centrifuged for 5 minutes and 5 µl of the supernatant was added into 45 µl of 100 mM of Tris buffer (pH 8.0). This crude genomic DNA extract was used as the template for PCR amplification.

Detection of the presence or absence of the $MSRA_2$ construct was achieved by performing a PCR reaction with the extracted genomic DNA and oligos # 3 and # 4 from Table 2 above. The expected size of the product from the reaction was 129 bp. This method allowed for the identification of transgenic tobacco and potato plants transformed with the $pDMSRA_2$ or $pRSHMSRA_2$ constructs.

Detection of the $MSRA_3$ construct was achieved by performing PCR reactions either with oligo #3 and oligo # 4 from Table 3 above or with a primer specific for the 2×35S CAMV promoter in combination oligo #4 from Table 3 above. Transgenic tobacco plants containing the $pDMSRA_3$ construct were identified.

A control plant was also engineered to contain a GUS gene under the control of a super promoter containing the mas (mannopine synthase) promoter/activator region preceded by a trimer of the ocs (octopine synthase) upstream activating sequence (Ni et al., *The Plant J.* 7: 661–676. 1995). The insertion of this transgene into the tobacco plant genome was confirmed via PCR techniques.

In some cases, active expression of the transgene was confirmed by Northern blot analysis. The RNA substrate for these experiments was isolated and purified from the transgenic tobacco and potato plants. The protocol used for this isolation was performed in accordance with Verwoerd et al., *Nucl. Acids Res.* 17:2362, 1989.

6. Resistance to Bacterial Pathogens

To examine the resistance of the transgenic potato and tobacco plants to the bacterial pathogen *Erwinia carotovora*, the bacteria were grown in LB media at RT overnight (A600=2.9). A 2 ml aliquote of *Erwinia* culture was diluted 5 times in $dH_2O$ and 1 ml of the diluted culture was added to 2 ml MS liquid media and used in the antibacterial assay. Freshly cut branches (~3.5 cm) from transgenic plants or control plants were inserted into the tubes containing the diluted *Erwinia* culture so that the bottom of the cut edge of the plant was immersed into the bacterial culture. The test tubes were incubated at RT at 3000 lux and observed intermittently.

Transgenic potato plants containing $pDMSRA_2$ and transgenic tobacco plants containing either $pDMSRA_2$ or $pRSHMSRA_2$ were tested as described and showed resistance to the pathogen. After one week of growth in the presence of the bacterial culture the transgenic plants were uninfected (as detennined by visual inspection) and continued to grow. In sharp contrast, a control plant challenged with bacterial culture was severely infected after one week of incubation, growth was inhibited and the plant died after 2–3 weeks of exposure to fungal pathogens.

To examine the resistance of transgenic potato tubers to the bacterial pathogen *Erwinia carolovora* cv *carotovora*, a small well was made into tuber discs (2 cm diameter, 3 cm thick). Twenty microliters of 100× diluted overnight bacterial culture (approximately $2×10^7$ CFU) was pipetted into the well and discs were incubated at room temperature for 6 days. Rotted tissue was then gently removed from the tuber discs and the loss of weight of the tissue determined. Results obtained from such assays showed that compared to the non-transgenic control the transgenic potato tissue is resistant to soft rot (FIG. 1).

Figure 2:
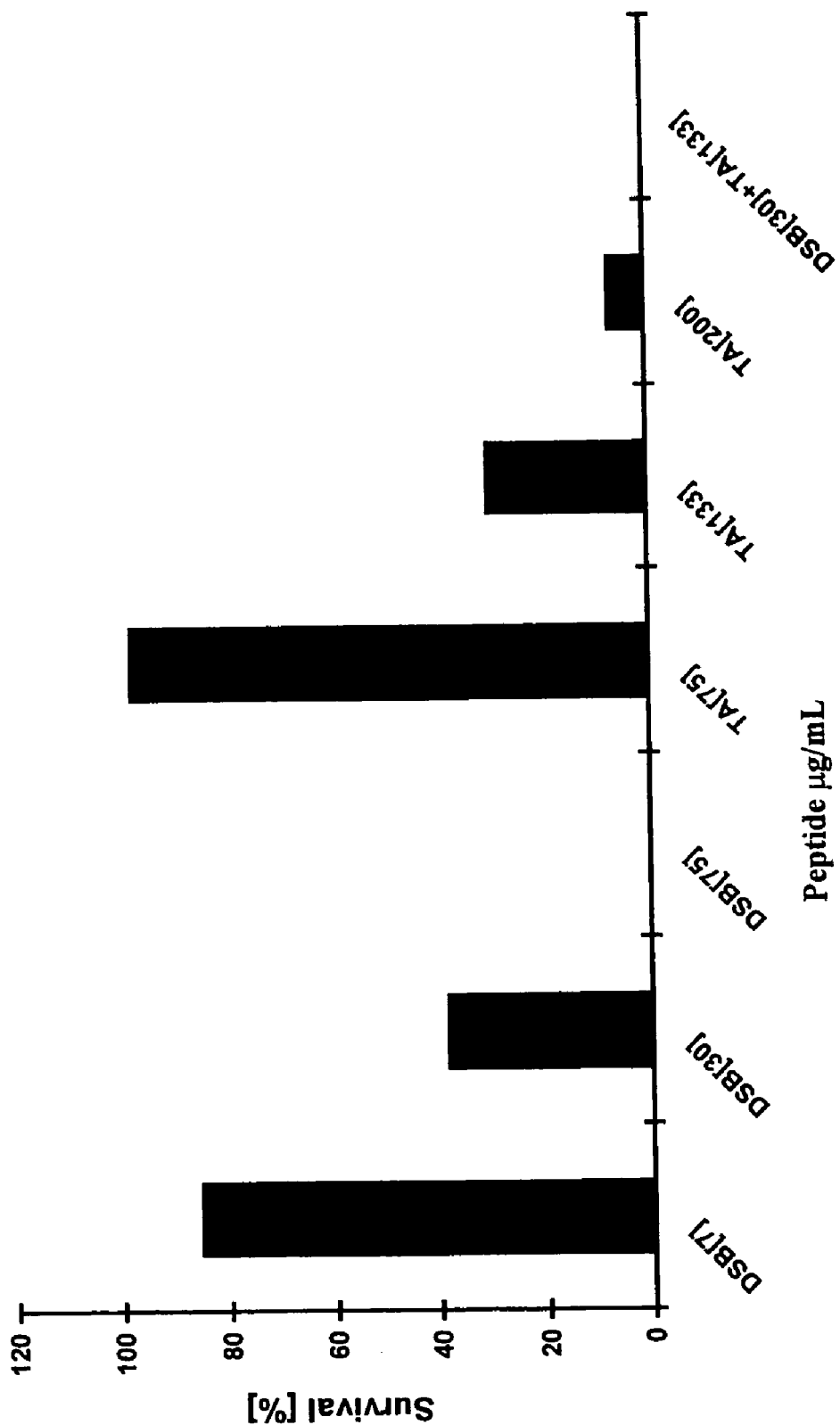
FIG. 2 is a graph that shows the bactericidal effect of the peptides $MSRA_2$ (Dermaseptin B) and $MSRA_3$ (Temporin A) on *E. coli*. The cell cultures were incubated at room temperature in the presence of indicated concentration of Dermaseptin B (DSB; 7 µg/ml, 30 µg/ml, and 75 µg/ml), Temporin A (TA; 75 µg/ml, 133 µg/ml, 200 µg/ml) and a combination of Temporin A and Dermaseptin B (133 µg/ml Temporin A and 30 µg/ml Dermaseptin B) for 4 hours, diluted and plated on LB plates. After overnight incubation at 37° C., the colonies were counted and the survival of bacteria was scored.
Figure 3:
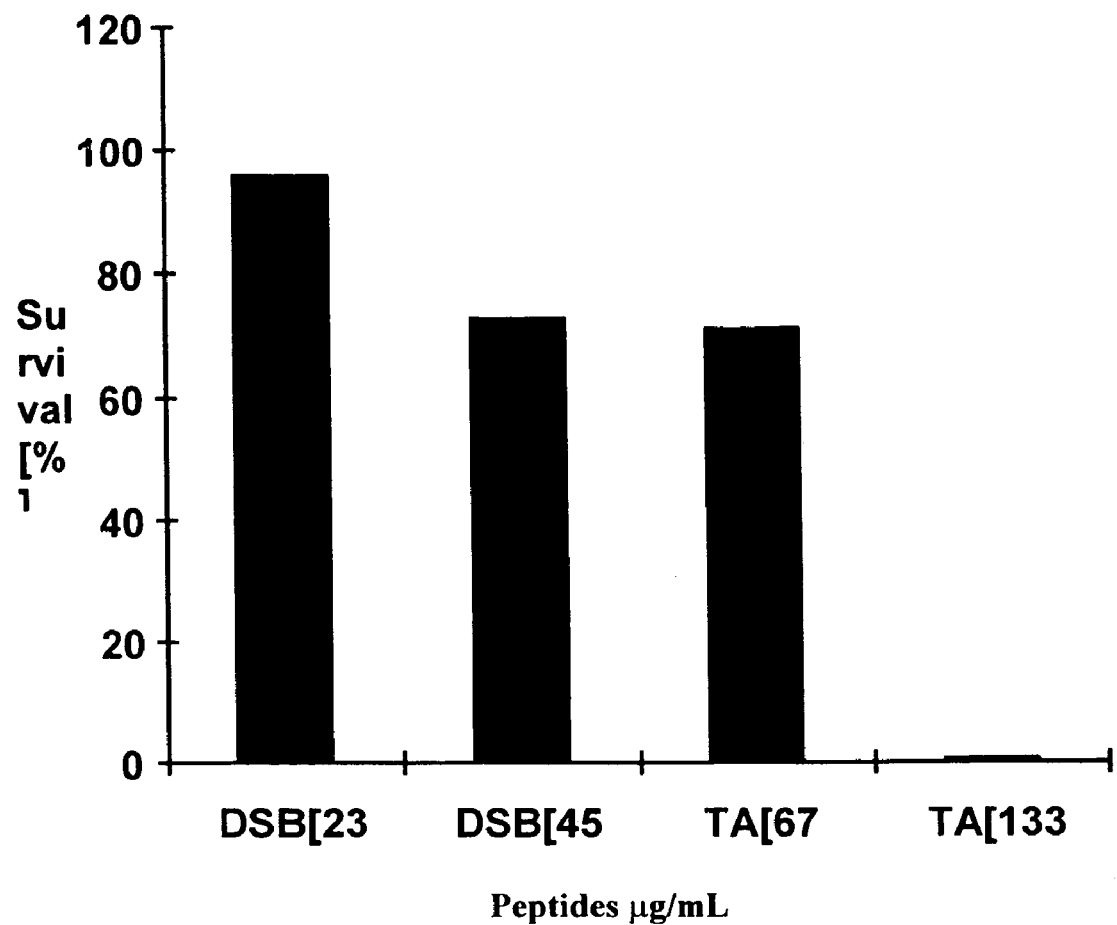
FIG. 3 is a graph that shows the bactericidal effect of the peptides $MSRA_2$ (Dermaseptin B) and $MSRA_3$ (Temporin A) on *E. carotovora*. The cell cultures were incubated at room temperature in the presence of indicated concentration of Dermaseptin B (DSB; 23 μg/ml, 45 μg/ml) or Temporin A (TA; 67 μg/ml, 133 μg/ml) for 4 hours, diluted and plated on LB plates. After overnight incubation at 28° C., the colonies were counted and the survival of bacteria was scored.

Bactericidal effects of antimicrobial peptides (SEQ ID NO: 34 ($MRSA_3$) and SEQ ID NO: 28 ($MRSA_2$)) were determined against *Escherichia coli* (FIG. 2) and *Erwinia carolovora* (FIG. 3) in microtiter plates in a final volume of 220 µl containing approximately $1×10^5$ bacteria/ml and indicated concentration of antimicrobial peptides. The cell cultures were incubated at room temperature for 4 hours, diluted and plated on LB plates. After overnight incubation at 37° C. (*E. coli*) or 28° C. (*E. carotovora*) the colonies were counted and the survival of bacteria was scored. Results from both assays showed that the peptides have significant antimicrobial activity.

7. Resistance to Fungi

Mature plants were tested for their resistance to various fungi using the following protocol. One $cm^2×0.5$ cm of *Fusarium* or *Phytophthora* sp. —containing media slices were cut and put in the center of fresh plates of V8 agar media (250 ml/L V8 juice, 7 grams/L agar) in a 9 cm petri dish and grown for about one month at room temperature, or until the fungal mycelia completely covered the petri dish. Shoots of transgenic plants (~10 cm) were cut and transferred into MS medium for further growth. According to different treatments, plants were allowed to grow for 3 days or 2 weeks until the shoots rooted. Two 1 $cm^2×0.5$ cm slices of the fungal agar were then applied to both sides of the plant shoots without wounding the plant. The resulting degree of infection was then determined visually.

In a representative experiment, a transgenic potato plant transformed with pDMSRA$_2$, tobacco plants transformed with either pRSHMRSA$_2$ or pDMSRA$_2$, and control potato and tobacco plants were exposed to *Phytophihora cactorum*. After 7 days, *Phytophthora cactorum* had grown over the surface of MS medium, and penetrated into the roots and the stems of the control plants, causing impairment of vital plant functions. It was apparent that the roots in the control plants were severely damaged. The interaction between plants and fungi caused the secretion of yellow-brown pigments indicative of the decay process. Subsequently, the plants lost water and leaves became curly, the bottom of the stems softened, and the roots died. However, the transgenic plants stayed healthy and had no disease symptoms even though the fungal mycelia completely covered the MS media.

The experiment described above was also used to test the transgenic plant's resistance to *Phytophlhora infestans*. The results from these assays showed that the transgenic plants were also resistant to *Phytophihora infestans*.

Another experiment was performed challenging a pDMSRA$_2$ transgenic potato plant with *Fusarium solani*. After 6 days, *Fusarium* grew all over the surface of MS medium, the damage to the roots in the control plants was severe, and the base of stem was penetrated by *Fusarium* and the stems were softened and veins of infected leaves showed clear browning and necrosis. After several days, the control plant collapsed and died. However, the transgenic plant continued to grow even under the extreme fungal infestation by *Fusarium solani*.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

REFERENCES

Ainley et al. (1993). *Plant Mol Biol.*, 22:13–23.
Allefs et al. (1996). *Mol. Breeding*, 2: 97–105.
Altschul et al. (1990). *J. Mol. Biol.*, 215:403–10
Altschul et al. (1994). *Nature Gene.*, 6:119–29.
Altschul et al. (1997). *Nucleic Acids Res.* 25:3389–3402.
Amiche et al. (1994). *J. Biol. Chem.* 269:1747–852.
An et al. (1988). *Plant Physiol.*, 88:547.
Anzai et al. (1989). *Mol. Gen. Genet.*, 219:492–494.
Ausubel et al., (1987). *Current Protocals in Molecular Biology*, Greene Publishing Associates and Wiley-Intersciences.
Baker et al. (1997). *Science*, 276: 726–733.
Beachey et al. (1990). *Ann. Rev. Phytopathology*, 28:451–474.
Benfey & Chua (1990). *Science*, 250:959–966.
Broglie et al. (1991). *Science*, 254:1194–1197.
Bustos et al. (1989). *Plant Cell*, 1:839.
Callis et al. (1988). *Plant Physiol.*, 88:965.
Carpenter et al. (1992). *The Plant Cell*, 4:557–571.
Chapentier et al. (1998). *Biol. Chem.* 273:14690–14697.
Chaudhary et al. (1989). *Nature* 339: 394–397.
Conrad and Fiedler (1994). *Plant Mol. Biol.*, 26:1023–1030.
Corpet et al. (1988). *Nucleic Acids Research*, 16:10881–90.
Daher et al. (1988). *Proc. Natl. Acad. Sci USA*, 85:7327–7331.
Datla et al. (1993). *Plant Sci.*, 94:139–149.
De Block, M. (1988). *Theoret. Appl. Genet.*, 76:767–774.
Dekeyser et al. (1990). *Plant Cell*, 2:591.
Del Sal et al. (1992). *Biochem. Biophys. Res. Commun.* 187:467–472.
Denis et al. (1993). *Plant Physiol.*, 101:1295–1304.
Düring (1996). *Mol. Breeding*, 2:297–305.
Eppel and Bohlmann (1997). *The Plant Cell*, 9: 509–520.
Fillati et al. (1987). *Bio/Technology*, 5:726–730.
Firek et al. (1993). *Plant Mol. Biol.*, 23:861–870.
Fischhoff et al. (1987). *Bio/Technology*, 5:807–814.
Florak et al. (1995). *Transgenic Res.*, 4:132–141
Fromm et al. (1989). *Plant Cell*, 1:977.
Gamborg et al. (1968). *Exp. Cell Res.*, 50:151–158.
Gan & Amansino (1995). *Science*, 270:1986–1988.
Gatz et al. (1997). *Plant Mol. Biol.*, 48:89–108.
Gelvin et al. (1990). *Plant Molecular Biology Manual*, Kluwer Academic Publishers.
Gilmartin et al. (1992). *The Plant Cell*, 4:839–949.
Hancock and Lehrer (1998). *TIBTECH.*, 16: 1–7
Higgins & Sharp (1988). *Gene*, 73:237–244.
Higgins & Sharp (1989). *CABIOS*, 5:151–153.
Huang, et al. (1992). *Computer Applications in the Biosciences*, 8: 55–65.
Innis et al. (1990). *PCR Protocols, A Guide to Methods and Applications*.
Jaynes (1993). *Plant Science*, 89:43–53.
Kay et al. (1987). *Science*, 236:1299–1302.
Keil et al. (1986). *Nucl. Acids. Res.*, 14: 5641–5650.
Kenny and Alcorn (1980). *Plant Dis.*, 64:674–676.
Kuhlemeier et al. (1989). *Plant Cell*, 1:471.
Langridge et al. (1989). *Bio/Technology*, 10:305–308.
Larrick et al. (1995). *Infect. Immun.* 63:1291–1297.
Mahoney et al., (1995). *FEBS Lett.* 377:519–522.
Marcotte et al. (1989). *Plant Cell*, 1: 471.
Mason et al. (1992). *Proc. Natl. Acad. Sci. U.S.A.*, 89:11745–11749.
Ni et al. (1995). *The Plant J.*, 7: 661–676
Mor & Nicolas (1994). *Journal Biochemical Chemistry*, 269:1934–39.
Mor. et al. (1991). *Biochemistry*, 30:8824–830.
Mor et al. (1994). *J. Biol. Chem.*, 269: 31635–31641
Murashige & Skoog (1962). *Physiol. Plant.*, 15:473–479.
Needleman & Wunsch (1970). *J. Mol. Biol.*, 48:443.
Odel et al. (1985). *Nature*, 313:810.
Odell et al. (1994). *Plant Physiol.*, 106:447–458.
Opperman et al. (1993). *Science*, 263:221–223.
Pearson & Lipman (1988). *Proc. Natl. Acad Sci. USA*, 85:2444.
Pearson et al. (1994). *Methods inMolecular Biology*, 24:307–31.
Perombelon and Kelman (1980). *Ann. Rev. Phytopathology*, 18:361–387.
Pouwels et al. (1987). *Cloning Vectors: A Laboratory Manual*, 1985, supp.
Roshal et al. (1987). *The EMBO J.*, 6:1155.
Sambrook et al., (1989). *Molecular Cloning: A Laboratory Manual*, Cold Spring Harbor.
Sanchez-Serrano et al. (1987). *The EMBO J.*, 6:303–306.
Sawyer, R. L. (1984). Potatoes for the developing world. Lima Peru International Potato Center.
Schaffner & Sheen (1991). *Plant Cell*, 3:997.
Schernthaner et al. (1988). *EMBO J.*, 7:1249.
Scott and Collins. (1996). *Blood* 88:2517–2530.
Shah et al. (1986). *Science*, 233:478.

Siebertz et al. (1989). *Plant Cell,* 1:961.
Simmaco et al. (1996). *Eur. J. Biochem.,* 242:788–92.
Skerlavaj et al. (1996). *J. Biol. Chem.* 271: 28375–381.
Smith & Waterman (1981). *Adv. Appl. Math.,* 2:482.
Stockhause et al. (1997). *The Plant Cell,* 9:479–489.
Strahilevitz (1994). *Biochemistry,* 33:10951–960.
Terada & Shimamoto (1990). *Mol. Gen. Genet.,* 220:389.
Terras et al. (1995). ) *The Plant Cell,* 7:573–588.
Tossi et al. (1995). *Eur. J. Biochem,* 15:941–6.
Vaeck et al. (1987). *Nature,* 328:33–37.
Verwoerd et al. (1989). *Nucl. Acids Res.,* 17:2362.
Wagner et al. (1987). *Proc. Natl. Acad. Sci. U.S.A.,* 84:2097–5100.
Wechselberger (1998). *Biochim. Biophys. Acta* 1388: 279–283.
Weise et al. (1994). *Plant Mol. Biol.,* 26:667–677.
Weising et al. (1988). *Ann. Rev. Genet.,* 22:421–477.
Weissbach & Weissbach (1989). *Methods for Plant Molecular Biology,* Academic Press, 5:173–184.
Yamamoto et al. (1990): *Plant Cell,* 3:371–382.
Zhao et al. (1995). *FEBS Lett.* 367:130–134.

SEQUENCE LISTING

```
<160> NUMBER OF SEQ ID NOS: 41

<210> SEQ ID NO 1
<211> LENGTH: 443
<212> TYPE: DNA
<213> ORGANISM: Phyllomedusa bicolor
<220> FEATURE:
<221> NAME/KEY: CDS
<222> LOCATION: (58)..(294)

<400> SEQUENCE: 1
ccacgcgtcc gattctgtcc tccagtactc aacacattct gaattgtaag aacaaac         57 atg gat atc ctg aag aaa tct ctt ttc ctt gta tta ttc ctt gga ttg      105
Met Asp Ile Leu Lys Lys Ser Leu Phe Leu Val Leu Phe Leu Gly Leu
1               5                   10                  15 gtt tcc ctt tcc atc tgt gaa gaa gag aaa aga gaa aat gaa gat gag      153
Val Ser Leu Ser Ile Cys Glu Glu Glu Lys Arg Glu Asn Glu Asp Glu
                20                  25                  30 gag aaa caa gat gac gag caa agt gaa atg aag aga gct atg tgg aaa      201
Glu Lys Gln Asp Asp Glu Gln Ser Glu Met Lys Arg Ala Met Trp Lys
            35                  40                  45 gat gtg tta aaa aaa ata gga aca gtg gcc tta cat gca gga aaa gcg      249
Asp Val Leu Lys Lys Ile Gly Thr Val Ala Leu His Ala Gly Lys Ala
        50                  55                  60 gct tta ggt gca gtt gct gat aca ata agt caa gga gag caa taa          294
Ala Leu Gly Ala Val Ala Asp Thr Ile Ser Gln Gly Glu Gln
65                  70                  75 agtgaaaaaa atttaaaatt gaattactct aaatagaaca attagcaata attgtgtcaa    354
acctacatta aagcatactg aaccaaaaaa aaaaaaaaaa aaaaaaaaaa aaaaaaaaa     414 aaaaaaaaaa aaaaaaaaa aaaaaaaa                                        443

<210> SEQ ID NO 2
<211> LENGTH: 78
<212> TYPE: PRT
<213> ORGANISM: Phyllomedusa bicolor

<400> SEQUENCE: 2

Met Asp Ile Leu Lys Lys Ser Leu Phe Leu Val Leu Phe Leu Gly Leu
1               5                   10                  15

Val Ser Leu Ser Ile Cys Glu Glu Glu Lys Arg Glu Asn Glu Asp Glu
                20                  25                  30

Glu Lys Gln Asp Asp Glu Gln Ser Glu Met Lys Arg Ala Met Trp Lys
            35                  40                  45

Asp Val Leu Lys Lys Ile Gly Thr Val Ala Leu His Ala Gly Lys Ala
        50                  55                  60

Ala Leu Gly Ala Val Ala Asp Thr Ile Ser Gln Gly Glu Gln
```

```
65                  70                  75

<210> SEQ ID NO 3
<211> LENGTH: 27
<212> TYPE: PRT
<213> ORGANISM: Phyllomedusa bicolor

<400> SEQUENCE: 3

Asp Val Leu Lys Lys Ile Gly Thr Val Ala Leu His Ala Gly Lys Ala
 1               5                  10                  15

Ala Leu Gly Ala Val Ala Asp Thr Ile Ser Gln
            20                  25

<210> SEQ ID NO 4
<211> LENGTH: 31
<212> TYPE: PRT
<213> ORGANISM: Phyllomedusa bicolor

<400> SEQUENCE: 4

Ala Met Trp Lys Asp Val Leu Lys Lys Ile Gly Thr Val Ala Leu His
 1               5                  10                  15

Ala Gly Lys Ala Ala Leu Gly Ala Val Ala Asp Thr Ile Ser Gln
            20                  25                  30

<210> SEQ ID NO 5
<211> LENGTH: 36
<212> TYPE: PRT
<213> ORGANISM: Pachymedusa dacnicolor

<400> SEQUENCE: 5

Gly Met Trp Ser Lys Ile Lys Asn Ala Gly Lys Ala Ala Ala Lys Ala
 1               5                  10                  15

Ser Lys Lys Ala Ala Gly Lys Ala Ala Leu Gly Ala Val Ser Glu Ala
            20                  25                  30

Leu Gly Glu Gln
        35

<210> SEQ ID NO 6
<211> LENGTH: 31
<212> TYPE: PRT
<213> ORGANISM: Pachymedusa dacnicolor

<400> SEQUENCE: 6

Ala Leu Trp Lys Thr Leu Leu Lys Lys Val Gly Lys Val Ala Gly Lys
 1               5                  10                  15

Ala Val Leu Asn Ala Val Thr Asn Met Ala Asn Gln Asn Glu Gln
            20                  25                  30

<210> SEQ ID NO 7
<211> LENGTH: 35
<212> TYPE: PRT
<213> ORGANISM: Agalychnis annae

<400> SEQUENCE: 7

Gly Met Trp Ser Thr Ile Arg Asn Val Gly Lys Ser Ala Ala Lys Ala
 1               5                  10                  15

Ala Asn Leu Pro Ala Lys Ala Ala Leu Gly Ala Ile Ser Glu Ala Val
            20                  25                  30

Gly Glu Gln
        35
```

```
<210> SEQ ID NO 8
<211> LENGTH: 29
<212> TYPE: PRT
<213> ORGANISM: Agalychnis annae

<400> SEQUENCE: 8

Gly Met Phe Thr Asn Met Leu Lys Gly Ile Gly Lys Leu Ala Gly Gln
1               5                   10                  15

Ala Ala Leu Gly Ala Val Lys Thr Leu Ala Gly Glu Gln
            20                  25

<210> SEQ ID NO 9
<211> LENGTH: 30
<212> TYPE: PRT
<213> ORGANISM: Agalychnis annae

<400> SEQUENCE: 9

Ser Leu Trp Ser Lys Ile Lys Glu Met Ala Ala Thr Ala Gly Lys Ala
1               5                   10                  15

Ala Leu Asn Ala Val Thr Gly Met Val Asn Gln Gly Glu Gln
            20                  25                  30

<210> SEQ ID NO 10
<211> LENGTH: 34
<212> TYPE: PRT
<213> ORGANISM: Phyllomedusa sauvagei

<400> SEQUENCE: 10

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 11
<211> LENGTH: 34
<212> TYPE: PRT
<213> ORGANISM: Phyllomedusa sauvagei

<400> SEQUENCE: 11

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 12
<211> LENGTH: 30
<212> TYPE: PRT
<213> ORGANISM: Phyllomedusa sauvagei

<400> SEQUENCE: 12

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30

<210> SEQ ID NO 13
<211> LENGTH: 27
<212> TYPE: PRT
<213> ORGANISM: Phyllomedusa sauvagei
```

-continued

```
<400> SEQUENCE: 13

Ala Leu Trp Met Thr Leu Leu Lys Lys Val Leu Lys Ala Ala Ala Lys
1               5                   10                  15

Ala Leu Asn Ala Val Leu Val Gly Ala Asn Ala
            20                  25

<210> SEQ ID NO 14
<211> LENGTH: 29
<212> TYPE: PRT
<213> ORGANISM: Phyllomedusa sauvagei

<400> SEQUENCE: 14

Gly Leu Trp Ser Lys Ile Lys Thr Ala Gly Lys Ser Val Ala Lys Ala
1               5                   10                  15

Ala Ala Lys Ala Ala Val Lys Ala Val Thr Asn Ala Val
            20                  25

<210> SEQ ID NO 15
<211> LENGTH: 329
<212> TYPE: DNA
<213> ORGANISM: Rana temporaria
<220> FEATURE:
<221> NAME/KEY: CDS
<222> LOCATION: (53)..(238)

<400> SEQUENCE: 15
cccctccagc tgtctacatt ctcataacca actgaaccac ccgagcccaa ag atg ttc      58
                                                         Met Phe
                                                         1 acc ttg aag aaa tcc ctc tta ctc ctt ttc ttc ctt ggg acc atc aac      106
Thr Leu Lys Lys Ser Leu Leu Leu Phe Phe Leu Gly Thr Ile Asn
        5                   10                  15 tta tct ctc tgt gag gaa gag aga gat gcc gat gaa gaa aga aga gat      154
Leu Ser Leu Cys Glu Glu Glu Arg Asp Ala Asp Glu Glu Arg Arg Asp
    20                  25                  30 gat ctc gaa gaa agg gat gtt gaa gtg gaa aag cga ttt ttt cca gtg      202
Asp Leu Glu Glu Arg Asp Val Glu Val Glu Lys Arg Phe Phe Pro Val
35                  40                  45                  50 att gga agg ata ctc aat ggt att ttg gga aaa taa ccaaaaaaag            248
Ile Gly Arg Ile Leu Asn Gly Ile Leu Gly Lys
                55                  60 ttaaaacttt ggaaatggaa ttggaaatca tctaatgtgg aatgtcattt agctaaatgc    308
acatcaaatg tcttataaaa a                                              329

<210> SEQ ID NO 16
<211> LENGTH: 61
<212> TYPE: PRT
<213> ORGANISM: Rana temporaria

<400> SEQUENCE: 16

Met Phe Thr Leu Lys Lys Ser Leu Leu Leu Phe Phe Leu Gly Thr
1               5                   10                  15

Ile Asn Leu Ser Leu Cys Glu Glu Glu Arg Asp Ala Asp Glu Glu Arg
            20                  25                  30

Arg Asp Asp Leu Glu Glu Arg Asp Val Glu Val Glu Lys Arg Phe Phe
        35                  40                  45

Pro Val Ile Gly Arg Ile Leu Asn Gly Ile Leu Gly Lys
    50                  55                  60

<210> SEQ ID NO 17
```

```
<211> LENGTH: 13
<212> TYPE: PRT
<213> ORGANISM: Rana temporaria

<400> SEQUENCE: 17

Phe Phe Pro Val Ile Gly Arg Ile Leu Asn Gly Ile Leu
1               5                   10

<210> SEQ ID NO 18
<211> LENGTH: 13
<212> TYPE: PRT
<213> ORGANISM: Rana temporaria

<400> SEQUENCE: 18

Phe Leu Pro Leu Ile Gly Arg Val Leu Ser Gly Ile Leu
1               5                   10

<210> SEQ ID NO 19
<211> LENGTH: 13
<212> TYPE: PRT
<213> ORGANISM: Rana temporaria

<400> SEQUENCE: 19

Leu Leu Pro Ile Val Gly Asn Leu Leu Lys Ser Leu Leu
1               5                   10

<210> SEQ ID NO 20
<211> LENGTH: 13
<212> TYPE: PRT
<213> ORGANISM: Rana temporaria

<400> SEQUENCE: 20

Leu Leu Pro Ile Leu Gly Asn Leu Leu Asn Gly Leu Leu
1               5                   10

<210> SEQ ID NO 21
<211> LENGTH: 13
<212> TYPE: PRT
<213> ORGANISM: Rana temporaria

<400> SEQUENCE: 21

Leu Leu Pro Ile Val Gly Asn Leu Leu Asn Ser Leu Leu
1               5                   10

<210> SEQ ID NO 22
<211> LENGTH: 13
<212> TYPE: PRT
<213> ORGANISM: Rana temporaria

<400> SEQUENCE: 22

Val Leu Pro Ile Ile Gly Asn Leu Leu Asn Ser Leu Leu
1               5                   10

<210> SEQ ID NO 23
<211> LENGTH: 13
<212> TYPE: PRT
<213> ORGANISM: Rana temporaria

<400> SEQUENCE: 23

Phe Leu Pro Leu Ile Gly Lys Val Leu Ser Gly Ile Leu
1               5                   10

<210> SEQ ID NO 24
<211> LENGTH: 12
<212> TYPE: PRT
```

```
<213> ORGANISM: Rana temporaria

<400> SEQUENCE: 24

Leu Ser Pro Asn Leu Leu Lys Ser Leu Leu Gly Lys
1               5                   10

<210> SEQ ID NO 25
<211> LENGTH: 10
<212> TYPE: PRT
<213> ORGANISM: Rana temporaria

<400> SEQUENCE: 25

Leu Leu Pro Asn Leu Leu Lys Ser Leu Leu
1               5                   10

<210> SEQ ID NO 26
<211> LENGTH: 13
<212> TYPE: PRT
<213> ORGANISM: Rana temporaria

<400> SEQUENCE: 26

Phe Val Gln Trp Phe Ser Lys Phe Leu Gly Arg Ile Leu
1               5                   10

<210> SEQ ID NO 27
<211> LENGTH: 99
<212> TYPE: DNA
<213> ORGANISM: Phyllomedusa bicolor
<220> FEATURE:
<221> NAME/KEY: CDS
<222> LOCATION: (1)..(99)

<400> SEQUENCE: 27 atg gcc atg tgg aaa gac gtt ctg aaa aag atc ggt act gtc gcc ctc      48
Met Ala Met Trp Lys Asp Val Leu Lys Lys Ile Gly Thr Val Ala Leu
1               5                   10                  15 cat gca ggg aag gcc gcg ctt gga gca gta gcc gac acc atc tcg cag      96
His Ala Gly Lys Ala Ala Leu Gly Ala Val Ala Asp Thr Ile Ser Gln
            20                  25                  30 taa                                                                  99

<210> SEQ ID NO 28
<211> LENGTH: 32
<212> TYPE: PRT
<213> ORGANISM: Phyllomedusa bicolor

<400> SEQUENCE: 28

Met Ala Met Trp Lys Asp Val Leu Lys Lys Ile Gly Thr Val Ala Leu
1               5                   10                  15

His Ala Gly Lys Ala Ala Leu Gly Ala Val Ala Asp Thr Ile Ser Gln
            20                  25                  30

<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence:PCR primer

<400> SEQUENCE: 29
atggccatgt ggaaagacgt tctgaaaaag atcggtactg tcgccctcca tgcaggg       57

<210> SEQ ID NO 30
<211> LENGTH: 63
```

-continued

<210> SEQ ID NO 30
<211> LENGTH: 63
<212> TYPE: DNA
<213> ORGANISM: Artificial Sequence
<220> FEATURE:
<223> OTHER INFORMATION: Description of Artificial Sequence:PCR primer

<400> SEQUENCE: 30
ttactgcgag atggtgtcgg ctactgctcc aagcgcggcc ttccctgcat ggagggcgac    60
agt                                                                 63

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 31
tctagaggta ccatggccat gtggaaagac g                                  31

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 32
caagcttctg cagagctctt actgcgagat ggtgtcgg                            38

<210> SEQ ID NO 33
<211> LENGTH: 60
<212> TYPE: DNA
<213> ORGANISM: Rana temporaria
<220> FEATURE:
<221> NAME/KEY: CDS
<222> LOCATION: (1)..(57)

<400> SEQUENCE: 33 atg gcc tct aga cat atg ttt ctg ccc cta atc ggg agg gtt ctc tcg    48
Met Ala Ser Arg His Met Phe Leu Pro Leu Ile Gly Arg Val Leu Ser
1               5                   10                  15 gga atc ctg taa                                                    60
Gly Ile Leu <210> SEQ ID NO 34
<211> LENGTH: 19
<212> TYPE: PRT
<213> ORGANISM: Rana temporaria

<400> SEQUENCE: 34

Met Ala Ser Arg His Met Phe Leu Pro Leu Ile Gly Arg Val Leu Ser
1               5                   10                  15
Gly Ile Leu

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence:PCR primer

<400> SEQUENCE: 35
atgtttctgc ccctaatcgg gagggttctc tcgggaatcc tgtaa                   45

<210> SEQ ID NO 36

-continued

```
<211> LENGTH: 45
<212> TYPE: DNA
<213> ORGANISM: Artificial Sequence
<220> FEATURE:
<223> OTHER INFORMATION: Description of Artificial Sequence:PCR primer

<400> SEQUENCE: 36
ttacaggatt cccgagagaa ccctcccgat tagggcaga aacat          45

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 37
ggtacctcta gacatatgtt tctgccccta                          30

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 38
ctgcagagct cttacaggat tcccgagag                           29

<210> SEQ ID NO 39
<211> LENGTH: 4
<212> TYPE: PRT
<213> ORGANISM: Phyllomedusa bicolor

<400> SEQUENCE: 39

Ala Met Trp Lys
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:spacer
      sequence

<400> SEQUENCE: 40

Ala Ser Arg His
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:spacer
      sequence

<400> SEQUENCE: 41

Ala Leu Trp Lys
1
```

The invention claimes is:

1. A transgenic plant comprising a recombinant nucleic acid molecule, wherein the nucleic acid molecule encodes a temporin A, B, F, G, or L peptide having temporin biological activity.

2. The transgenic plant of claim 1, wherein the nucleic acid molecule comprises SEQ ID NO: 15.

3. The transgenic plant of claim 1, wherein the temporin peptide comprises an amino acid sequence selected from the group consisting of SEQ ID NOS: 17, 18, 19, 23 and 26.

4. The transgenic plant of claim 3, wherein the temporin peptide further comprises an N terminal peptide extension of between 2 and 25 amino acids in length.

5. The transgenic plant of claim 4, wherein the N-terminal peptide extension is AMWK (SEQ ID NO: 39), ASRH (SEQ ID NO: 40), or ALWK (SEQ ID NO: 41).

6. A transgenic plant comprising a recombinant nucleic acid molecule, wherein the nucleic acid molecule encodes a fusion peptide having a formula P-T, wherein T is a temporin A, B, F, G, or L peptide and P is an anionic pro-region peptide.

7. A transgenic plant comprising a recombinant nucleic acid molecule, wherein the nucleic acid molecule encodes a fusion peptide having a formula P-S-T, wherein T is a temporin A, B, F, G, or L peptide, P is an anionic pro-region peptide and S is a spacer peptide.

8. A transgenic plant comprising a nucleic acid molecule encoding a peptide comprising an amino acid sequence selected from the group consisting of:
  (a) SEQ IDs: 17, 18, 19, 23 and 26 and fragments thereof;
  (b) amino acid sequences that differ from an amino acid sequence specified in (a) by one or more conservative amino acid substitutions; and
  (c) amino acid sequences that share at least 70% sequence identity with an amino acid sequence specified in (a), wherein the peptide has temporin biological activity.

9. The transgenic plant of claim 8, wherein the peptide further comprises an anionic pro-region peptide operably linked to the N-terminus of the peptide.

10. A transgenic plant comprising a recombinant nucleic acid molecule encoding a peptide comprising SEQ ID NO: 34.

11. The transgenic plant of claim 8, wherein the amino acid sequence shares at least 95% sequence identity to SEQ ID NO: 17, 18, 19, 23 or 26.

12. A transgenic plant comprising a recombinant nucleic acid molecule, wherein the recombinant nucleic acid molecule comprises SEQ ID NO: 33.

13. A transgenic plant expressing a temporin peptide, wherein the temporin peptide comprises SEQ ID NO: 18.

14. The transgenic plant of claim 4, wherein the N terminal peptide extension comprises MAMWK (amino acids 1–5 of SEQ ID NO: 28) or MASRH (amino acids 1–5 of SEQ ID NO: 33).

15. The transgenic plant of claim 3, wherein the peptide comprises the amino acid sequence shown in SEQ ID NO: 17.

16. The transgenic plant of claim 3, wherein the peptide comprises the amino acid sequence shown in SEQ ID NO: 19.

17. The transgenic plant of claim 3, wherein the peptide comprises the amino acid sequence shown in SEQ ID NO: 23.

18. The transgenic plant of claim 3, wherein the peptide comprises the amino acid sequence shown in SEQ ID NO: 26.

19. The transgenic plant of claim 8, wherein the amino acid sequence comprises SEQ ID NO: 17, 18, 19, 23, or 26 with one conservative amino acid substitution.

20. The transgenic plant of claim 9, wherein the anionic pro-region peptide comprises SEQ ID NO: 16.

21. The transgenic plant of claim 7, wherein the spacer peptide comprises between 2 and 25 amino acids.

22. The transgenic plant of claim 7, wherein the spacer peptide comprises SEQ ID NO: 41.

23. The transgenic plant of claim 6, wherein the temporin peptide comprises SEQ ID NO: 17, 18, 19, 23, or 26.

24. The transgenic plant of claim 7, wherein the temporin peptide comprises SEQ ID NO: 17, 18, 19, 23, or 26.

25. The transgenic plant of claim 1, wherein the plant is a tobacco plant or a potato plant.

26. The transgenic plant of claim 1, wherein the plant is resistant to bacteria or fungi.

27. The transgenic plant of claim 25, wherein the bacteria is *E. carotovora* or *E. coli*.

28. The transgenic plant of claim 25, wherein the fungi is a *Fusarium* sp. or a *Phytophthora* sp.

29. The transgenic plant of claim 8, wherein the amino acid sequence shares at least 80% sequence identity to SEQ ID NO: 17, 18, 19, 23, or 26.

30. The transgenic plant of claim 8, wherein the amino acid sequence shares at least 85% sequence identity to SEQ ID NO: 17, 18, 19, 23, or 26.

31. The transgenic plant of claim 8, wherein the amino acid sequence shares at least 90% sequence identity to SEQ ID NO: 17, 18, 19, 23, or 26.

32. The transgenic plant of claim 1, wherein the temporin peptide consists of SEQ ID NO: 17, 18, 19, 23, or 26.

* * * * *

UNITED STATES PATENT AND TRADEMARK OFFICE
CERTIFICATE OF CORRECTION

PATENT NO. : 7,081,568 B2
APPLICATION NO. : 10/719623
DATED : July 25, 2006
INVENTOR(S) : Misra et al.

It is certified that error appears in the above-identified patent and that said Letters Patent is hereby corrected as shown below:

In the Drawings:

In Figure 1, "Lost of w ight [%]" should be --Lost of weight [%]--.

In the Specification:

Column 3, line 3, "ID) NO: 34)." should be --ID NO: 34).--.

Column 3, line 18, "r" should be --or--.

Column 8, line 14, "samples, are" should be --samples are--.

Column 8, line 30, "20 $\mu L^{-1}$" should be --20 $gL^{-1}$--.

Column 14, line 22, "inton Plants" should be --into Plants--.

Column 15, line 58, "synihase" should be --synthase--.

Column 16, line 2, "et al." should be --et al.,--.

Column 16, line 8, "et al." should be --et al.,--.

Column 16, line 9, "et al." should be --et al.,--.

Column 16, line 11, "et al." should be --et al.,--.

Column 16, line 11, "*Biol.*" should be --*Biol.,*--.

Column 16, line 18, "Schemthaner" should be --Schernthaner--.

Column 16, line 51, "Agrobaclerium" should be --Agrobacterium--.

Column 19, line 25, "GATTAG" should be --GAT TAG--.

Column 19, line 30, "ATTCTC" should be --ATT CTC--.

Column 19, line 43 (specification page 29, line 7), "CAMV" should be --CaMV--.

Column 19, line 58, "timer" should be --trimer--.

Column 19, line 66, "dennaseptin" should be --dermaseptin--.

UNITED STATES PATENT AND TRADEMARK OFFICE
CERTIFICATE OF CORRECTION

PATENT NO. : 7,081,568 B2
APPLICATION NO. : 10/719623
DATED : July 25, 2006
INVENTOR(S) : Misra et al.

It is certified that error appears in the above-identified patent and that said Letters Patent is hereby corrected as shown below:

Column 21, line 20, "expenments" should be --experiments--.

Column 21, line 61, "CAMV" should be --CaMV--.

Column 22, line 28, "detennined" should be --determined--.

Column 22, line 34, "*carolovora*" should be --*carotovora*--.

Column 22, line 47, "*carolovora*" should be --*carotovora*--.

Column 23, line 7, "*Phytophihora*" should be --*Phytophthora*--.

Column 23, line 20, "*Phytophlhora*" should be --*Phytophthora*--.

Column 23, line 22, "*Phytophihora*" should be --*Phytophthora*--.

Column 24, line 24, "8: 55-65" should be --8: 155-65--.

Column 41, line 1, "claimes" should be --claimed--.

Signed and Sealed this

First Day of May, 2007

JON W. DUDAS
*Director of the United States Patent and Trademark Office*